US012109190B2

(12) United States Patent
Singh et al.

(10) Patent No.: US 12,109,190 B2
(45) Date of Patent: Oct. 8, 2024

(54) UROLITHINS AS IMMUNE RESPONSE ENHANCERS

(71) Applicant: Amazentis SA, Lausanne (CH)

(72) Inventors: Anurag Singh, Crissier (CH); Davide D'Amico, Renens (CH); Penelope Andreux, Eclepens (CH); William Blanco-Bose, La Croix (CH); Christopher L. Rinsch, Morges (CH)

(73) Assignee: Amazentis SA, Lausanne (CH)

( * ) Notice: Subject to any disclaimer, the term of this patent is extended or adjusted under 35 U.S.C. 154(b) by 232 days.

(21) Appl. No.: 17/822,027

(22) Filed: Aug. 24, 2022

(65) Prior Publication Data

US 2023/0097072 A1 Mar. 30, 2023

Related U.S. Application Data

(62) Division of application No. 17/061,265, filed on Oct. 1, 2020, now Pat. No. 11,426,380, which is a division
(Continued)

(30) Foreign Application Priority Data

Apr. 30, 2018 (GB) ..................................... 1807051
May 14, 2018 (GB) ..................................... 1807819

(51) Int. Cl.
*A61K 31/37* (2006.01)
*A61K 31/335* (2006.01)
(Continued)

(52) U.S. Cl.
CPC ............ *A61K 31/37* (2013.01); *A61K 31/335* (2013.01); *A61K 39/0011* (2013.01);
(Continued)

(58) Field of Classification Search
CPC ...... A61K 2039/55; A61K 2039/55511; A61K 2300/00; A61K 31/335; A61K 31/366;
(Continued)

(56) References Cited

U.S. PATENT DOCUMENTS 10,792,276 B2  10/2020  Singh et al.
11,426,380 B2   8/2022  Singh et al.
(Continued)

OTHER PUBLICATIONS

Fesus et al., "Autophagy Shapes Inflammation," Antioxidants & Redox Signaling, 14(11):2233-2243 (2011).
(Continued)

*Primary Examiner* — Savitha M Rao
(74) *Attorney, Agent, or Firm* — Foley Hoag LLP; Dana M. Gordon; Lawrence P. Tardibono

(57) ABSTRACT

Disclosed are compounds for use in raising an immune response to an antigen and/or enhancing, modulating or augmenting an immune response to an antigen. Particularly the use of urolithins. The invention also relates to immune enhancers comprising urolithins, methods of using such immune enhancers and processes for the preparation of such immune enhancers. The invention also relates to the use of urolithins in methods for modulating stem cell function, for example, enhancing stem cell numbers, promoting stem cell regeneration and promoting stem cell differentiation.

20 Claims, 6 Drawing Sheets

Related U.S. Application Data of application No. 16/398,956, filed on Apr. 30, 2019, now Pat. No. 10,792,276.

(51) Int. Cl.
| | |
|---|---|
| *A61K 39/00* | (2006.01) |
| *A61K 39/145* | (2006.01) |
| *A61K 39/39* | (2006.01) |
| *A61P 1/04* | (2006.01) |
| *A61P 1/16* | (2006.01) |
| *A61P 1/18* | (2006.01) |
| *A61P 13/12* | (2006.01) |
| *A61P 17/00* | (2006.01) |
| *A61P 19/02* | (2006.01) |
| *A61P 19/08* | (2006.01) |
| *A61P 21/00* | (2006.01) |
| *A61P 31/16* | (2006.01) |
| *A61P 35/00* | (2006.01) |
| *C07D 311/80* | (2006.01) |

(52) U.S. Cl.
CPC ............ *A61K 39/145* (2013.01); *A61K 39/39* (2013.01); *A61P 31/16* (2018.01); *A61K 2039/55* (2013.01); *A61K 2039/55511* (2013.01); *A61P 1/04* (2018.01); *A61P 1/16* (2018.01); *A61P 1/18* (2018.01); *A61P 13/12* (2018.01); *A61P 17/00* (2018.01); *A61P 19/02* (2018.01); *A61P 19/08* (2018.01); *A61P 21/00* (2018.01); *A61P 35/00* (2018.01); *C07D 311/80* (2013.01)

(58) Field of Classification Search
CPC .... A61K 31/37; A61K 39/00; A61K 39/0011; A61K 39/12; A61K 39/145; A61K 39/39; A61P 1/04; A61P 1/16; A61P 1/18; A61P 13/12; A61P 17/00; A61P 19/02; A61P 19/08; A61P 21/00; A61P 31/16; A61P 35/00; C07D 311/80; Y02A 50/30
See application file for complete search history.

(56) References Cited

U.S. PATENT DOCUMENTS

| | | |
|---|---|---|
| 2012/0264819 A1 | 10/2012 | Seeram et al. |
| 2014/0018415 A1 | 1/2014 | Rinsch et al. |
| 2017/0304263 A1 | 10/2017 | Pezzuto |
| 2019/0328703 A1 | 10/2019 | Singh et al. |
| 2021/0085642 A1 | 3/2021 | Singh et al. |

OTHER PUBLICATIONS

Invitation to Pay Additional Fees for International Application No. PCT/EP2019/061093 dated Jul. 29, 2019.
Tomas-Barberan et al., "Urolithins, the rescue of "old" metabolites to understand a "new" concept: Metabotypes as a nexus among phenolic metabolism, microbiota dysbiosis, and host health status," Mol Nutr Food Res, 61(1):1-35 (2017).

UROLITHINS AS IMMUNE RESPONSE ENHANCERS

RELATED APPLICATIONS

This application is a divisional of U.S. patent application Ser. No. 17/061,265, filed Oct. 1, 2020, now U.S. Pat. No. 11,426,380; which is a divisional of U.S. patent application Ser. No. 16/398,956, filed Apr. 30, 2019, now U.S. Pat. No. 10,792,276; which claims the benefit of priority to GB Patent Application No. 1807051.6, filed Apr. 30, 2018; and GB Patent Application No. 1807819.6, filed May 14, 2018.

FIELD

The present invention relates to compounds for use in raising an immune response to an antigen and/or enhancing, modulating or augmenting an immune response to an antigen. Particularly the use of urolithins. The invention also relates to immune enhancers comprising urolithins, methods of using such immune enhancers and processes for the preparation of such immune enhancers. The invention also relates to the use of urolithins in methods for modulating stem cell function, for example enhancing stem cell numbers, promoting stem cell regeneration and promoting stem cell differentiation.

BACKGROUND

Viruses cause a wide range of human diseases, ranging from acute self-resolving conditions to acute fatal diseases, such as rabies, measles, diarrheal diseases, hepatitis, polio, cold sores, HIV, ebola, zika and influenza. These microscopic particles spread easily, typically via person-to-person contact or touching contaminated surfaces. Once inside the body, viruses enter cells and reproduce quickly. Effective antiviral medications exist for only a few of the many human viral diseases. In many cases, treatment for a viral illness involves relieving symptoms until the body's immune system clears the infection.

Influenza poses a heavy burden to health services, causing significant morbidity and mortality in older people, very young children and people with chronic illness. The World Health Organisation estimates that seasonal influenza causes 250,000 to 500,000 deaths worldwide each year. Non-influenza-related viral respiratory tract infection is also a common illness in humans and also represent a significant health burden for the health service [Fendrick et al (2003) Arch. Intern. Med. 163(4), 487-94].

Bacterial diseases also represent a significant health burden. One of the bacterial diseases with the highest disease burden is tuberculosis, caused by the bacterium *Mycobacterium tuberculosis*, which kills about 2 million people a year, mostly in sub-Saharan Africa. Pathogenic bacteria contribute to other globally important diseases, such as pneumonia, which can be caused by bacteria such as *Streptococcus* and *Pseudomonas*, and foodborne illnesses, which can be caused by bacteria such as *Shigella, Campylobacter*, and *Salmonella*. Pathogenic bacteria also cause infections such as tetanus, typhoid fever, diphtheria, syphilis, and leprosy. Pathogenic bacteria are also the cause of high infant mortality rates in developing countries.

Vaccination with an inactivated or attenuated form of the causative pathogenic agent is a way to build up cellular (T cell—cytokine and memory) and humoral (B cell-antibody) immune responses in a host to counteract the harmful burden of being exposed to a pathogen. A prime example of a global vaccination strategy relates to immunisation with a flu vaccine. Each year there is the potential of yearly exposure to different strains of the Influenza virus leading to an incidence of upper respiratory tract infection (flu) and in advanced cases even life-threatening pneumonia and each year there is the opportunity to be immunised with a flu vaccine directed to the year's most prevalent strains. Studies have shown that the elderly >65+years with declining immune function and health status because of ageing are the most susceptible to exposure to the flu strains with incidence >30% in the US elderly population alone compared to <10% for healthy adult populations (18-49 yrs.) that have a robust immune system (CDC, 2011-2012 https://www.cdc.gov/mmwr/preview/mmwrhtml/mm6122a4.htm).

The flu vaccination works, but it is far from being effective with seasonal effectiveness rates being dependent on the type of vaccine and adjuvant used, the age of the person vaccinated, and the virulence of the pre-dominant strain of that season. On average in the US general population, effectiveness rates have varied between 10-60% with elderly having a high benefit of the vaccination but showing even lower effectiveness rates than the average due to lower immune function status (N Engl J Med. 2007 Oct. 4; 357(14):1373-81 and Interim Estimates of 2017-18 Seasonal Influenza Vaccine Effectiveness—United States, February 2018.MMWR Morb Mortal Wkly Rep. 2018 Feb. 16; 67(6): 180-185)

Ageing is associated with immunosenescence and inflammaging (Aging Clin Exp Res. 2009 June; 21(3):201-9; Front Immunol. 2018 Jan. 10; 8:1960. doi: 10.3389/fimmu.2017.01960). With the decline in immune function and health with ageing, comes a greater risk associated with being impacted by an infectious agent and disease leading to a higher mortality and morbidity rate in the elderly. The ageing population is anticipated to account for >25% of the world's population by 2030 (United Nations, Department of Economic and Social Affairs, Population Division (2015). World Population Ageing 2015 (ST/ESA/SER.A/390)) and maintaining or preventing the decline of the immune function is key to maintaining a good quality of life in this population. In addition, decline in immune function leads to decreased efficiency in response to vaccination in a population most at risk of developing diseases such as flu.

Ageing is thought to be in part due to the ageing of the self-renewing stem cells of an organism and the decline in the number of stem cells. This ageing of stem cells is thought to be due to intrinsic events such as DNA damage, as well as extrinsic events such as changes in the stem cell niches or protected environments, which support the stem cells. Various niches have been shown to decline with age, thus even in the absence of significant effects of ageing on the quiescent stem cell population, stem-cell functionality could be compromised due to a decline of signals from the local niche, which regulate the function of stem cells and their progeny.

The decline in stem cell function refers to a decline in the common molecular processes underlying the core stem cell properties of self-renewal and the generation of differentiated progeny (D. Melton, in Essentials of Stem Cell Biology (Third Edition). (Academic Press, Boston, 2014), pp. 7-17.) This decline in stem cell function, self-renewal and stem cell number is thought to play a role in age-associated conditions such as frailty, atherosclerosis, and type 2 diabetes (Sharpless, 2007 Nat Rev Mol Cell Biol 2007 September; 8(9): 703-13). The role of ageing in stem cells has best been studied in the haematopoietic system, in which stem cells can be isolated to near homogeneity and their function can be studied using validated assays.

The haematopoietic system is composed of all the cellular components found in blood (FIG. 1A). The cells of the haematopoietic system require constant renewal, with approximately $10^{11}$-$10^{12}$ new blood cells needing to be produced daily in order to maintain steady state cellular levels in the average human. The production of these cells occurs in the organs of the haematopoietic system, spleen and bone marrow with all the different lineages being derived from multipotent progenitor cells (MPPs). The population of multipotent progenitor cells (MPPs) that maintain the blood cell system, are themselves maintained by haematopoietic stem cells (HSCs) (FIG. 1B). These cells can be identified by the expression of different proteins on their cell surface. As shown in FIG. 1B, the HSCs and the various MPP progenitor cell types have different combinations of cell surface proteins and by using different antibodies to these cell surface proteins, these different cells can be identified and isolated. The HSCs are stem cells that cycle infrequently and are able to maintain the more regularly cycling MPP populations. The infrequent cycling of the HSC population serves to protect these cells from DNA damage and maintain them for the life of the organism. Their depletion and the deterioration of the supporting HSC niche is thought to be important in ageing.

In bone marrow transplantation, the age of the donors HSCs used to reconstitute the blood cell system of the host, plays an important role in the success of the transplantation. Aged HSC's have been shown to be compromised in their ability to engraft and reconstitute the bone marrow (Stem Cells Transl Med. 2015 February; 4(2):186-94).

The deficiencies in the immune response during ageing demonstrate that there is a high level of need for new immune enhancers, in general, and in particular for populations with deficient immune systems, such as the elderly and children where the immune system is still developing. Compounds of formula (I), the subject of this patent, can serve as such an immune enhancer.

Urolithins are natural gut metabolites, produced by the host gut microflora upon exposure to dietary precursors (such as ellagitannins) that are found in high quantities in certain fruits and nuts such as pomegranate, berries and walnuts. Urolithin production in the gut shows a large human inter-individual variability and this has been associated with differences in the colon microbiota [Garcia-Villalba et al (2013) J. Agric. Food Chem., 2013, 61, 8797-8806]. Some studies have shown health benefits from the consumption of these polyphenol-rich fruits, the results across these studies are not consistent, possibly due to the large variation in the gut microbiota between individuals, which will result in different metabolite profiles greatly influencing their bio-potency. This raises another major challenge in designing optimal dietary intervention and limits the interpretation of studies investigating health aspects of the consumption of polyphenol-rich fruits. [for example, see Tomás-Barberán F A et al (2014) J Agric Food Chem. 62(28):6535-8 and González-Sarrías et al (2017) Mol Nutr Food Res. 61(5). doi: 10.1002/mnfr.201600830].

SUMMARY OF THE INVENTION

According to a first aspect of the invention, there is provided a compound of formula (I)

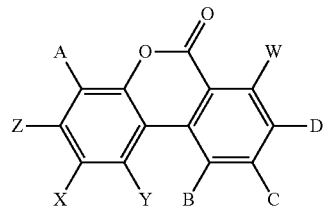

wherein:
A, B, C, D, W, X, Y and Z are each independently selected from H and OH;
or a salt thereof;
for use in (i) raising an immune response to an antigen and/or (ii) enhancing, modulating or augmenting an immune response to an antigen in a human or animal subject.

Urolithins, such as urolithin A, are now surprisingly believed to boost immune function and health by improving immune cellular and antibody (humoral) responses. Urolithins, such as Urolithin A, can be used to keep the immune system functioning optimally and as an added intervention, prior to vaccination to substantially boost the effectiveness of current vaccines, particularly in susceptible population such as the elderly or children.

According to a further aspect of the invention there is provided the use of a compound of formula (I) in the manufacture of a medicament for (i) raising an immune response to an antigen and/or (ii) enhancing, modulating or augmenting an immune response to an antigen in a human or animal subject.

According to a further aspect of the invention there is provided a method of (i) raising an immune response to an antigen and/or (ii) enhancing, modulating or augmenting an immune response to an antigen in a human or animal subject which comprises the administration of an effective amount of a compound of formula (I).

According to a further aspect of the invention there is provided a method of (i) raising an immune response to an antigen and/or (ii) enhancing, modulating or augmenting an immune response to an antigen in a human or animal subject which comprises the administration of an effective amount of a compound of formula (I) as an immune enhancer.

According to a further aspect of the invention there is provided a compound of formula (I) for use in a method of improving immune function and/or immune health in a human or animal subject.

According to a further aspect of the invention there is provided a compound of formula (I) for use in a method of improving immune function and/or immune health in a human or animal subject when administered as an immune enhancer.

According to a further aspect of the invention there is provided the use of a compound of formula (I) in the manufacture of a medicament for use in a method of improving immune function and/or immune health in a human or animal subject.

According to a further aspect of the invention there is provided a method of improving immune function and/or immune health which comprises the administration of an effective amount of a compound of formula (I).

According to a further aspect of the invention there is provided a compound of formula (I) for use in a method for boosting the immune system.

According to a further aspect of the invention there is provided the use of a compound of formula (I) in the manufacture of a medicament for boosting the immune system.

According to a further aspect of the invention there is provided a method of boosting the immune system comprising administration of an effective amount of a compound of formula (I).

According to a further aspect of the invention there is provided a compound of formula (I) for use in a method for modulating the immune system.

According to a further aspect of the invention there is provided the use of a compound of formula (I) in the manufacture of a medicament for modulating the immune system.

According to a further aspect of the invention there is provided a method of modulating the immune system comprising administration of an effective amount of a compound of formula (I).

In one embodiment, modulating an immune system comprises enhancing an immune response. In another embodiment, modulating an immune system comprises modulating an inflammatory response. In a further embodiment, modulating an immune response comprises enhancing an immune response and modulating an inflammatory response.

According to a further aspect of the invention there is provided a compound of formula (I) for use in a method of treating immunodeficiency in a human or animal subject.

According to a further aspect of the invention there is provided the use of a compound of formula (I) in the manufacture of a medicament for use in a method of treating immunodeficiency in a human or animal subject.

According to a further aspect of the invention there is provided a method of improving immune function and/or immune health which comprises the administration of an effective amount of a compound of formula (I) to a human or animal subject.

Inflamm-ageing plays a role in the rate of ageing and age-related disease and is a chronic progressive increase in pro-inflammatory status Inflammation is a series of complex response events which are caused by the host system facing a pathogen infection or various types of tissue injury. In common conditions, inflammatory responses disappear when proinflammatory factors in infection and tissue injuries are eliminated and then change into a highly active and well regulated balanced state, which is called resolving inflammation. However, in some circumstances, such as during ageing, inflammation fails to move into a steady state of anti-infection and tissue injury repair; instead the inflammation continues and moves to a non-resolving inflammation state.

According to a further aspect of the invention there is provided a compound of formula (I) for use in a method of treating inflamm-ageing in a human or animal subject. According to a further aspect of the invention there is provided a compound of formula (I) for use in a method of preventing, reducing or slowing inflamm-ageing in a human or animal subject.

According to a further aspect of the invention there is provided the use of a compound of formula (I) in a method of treating inflamm-ageing. According to a further aspect of the invention there is provided a compound of formula (I) in a method of preventing, reducing or slowing inflamm-ageing.

According to a further aspect of the invention there is provided a method of treating inflamm-ageing which comprises the administration of an effective amount of a compound of formula (I) to a human or animal subject. According to a further aspect of the invention there is provided a method of preventing, reducing or slowing inflamm-ageing which comprises the administration of an effective amount of a compound of formula (I) to a human or animal subject.

Measuring the ratio of interleukin 10 (IL10) to interleukin 12 (IL12) is a useful measure of the inflammatory phenotype of a cell, with a higher IL10/IL12 ratio indicating a more anti-inflammatory phenotype. Therefore, according to a further aspect of the invention there is provided a method of increasing the IL10/IL12 ratio using a compound of formula (I).

Compounds of the invention are also believed to be useful in the treatment of inflammatory disorders such as Behçet's disease. Therefore, according to a further aspect of the invention there is provided a compound of formula (I) for use in a method of treating Behçet's disease.

According to a further aspect of the invention there is provided a compound of formula (I) for use in a method of treating immunosenescence in a human or animal subject.

According to a further aspect of the invention there is provided the use of a compound of formula (I) in a method of treating immunosenescence.

According to a further aspect of the invention there is provided a method of treating immunosenescence which comprises the administration of an effective amount of a compound of formula (I) to a human or animal subject.

According to a further aspect of the invention there is provided a compound of formula (I) for use in a method of preventing, reducing or slowing stem cell senescence in a human or animal subject.

According to a further aspect of the invention there is provided the use of a compound of formula (I) in a method of preventing, reducing or slowing stem cell senescence.

According to a further aspect of the invention there is provided a method of preventing, reducing or slowing stem cell senescence which comprises the administration of an effective amount of a compound of formula (I) to a human or animal subject.

Immunosenescence may be due to ageing in haematopoietic stem cells which differentiate into cells of the immune system, therefore, according to a further aspect of the invention there is provided a compound of formula (I) for use in a method of treating stem cell ageing in a human or animal subject, particularly ageing of haematopoietic stem cells.

According to a further aspect of the invention there is provided the use of a compound of formula (I) in the manufacture of a medicament for use in a method of treating stem cell ageing in a human or animal subject, particularly ageing of haematopoietic stem cells.

According to a further aspect of the invention there is provided a method of treating stem cell ageing, particularly ageing of haematopoietic stem cells which comprises the administration of an effective amount of a compound of formula (I) to a human or animal subject.

According to a further aspect of the invention, there is provided a compound of formula (I) for use in a method of increasing the number of CD34 negative haematopoietic stem cells.

According to a further aspect of the invention, there is provided a compound of formula (I) for use in a method of increasing the number of CD34 negative haematopoietic stem cells and CD34 positive, CD 48 negative haematopoietic progenitor cells.

According to a further aspect of the invention, there is provided a compound of formula (I) for use in a method of increasing the number of CD34 positive haematopoietic progenitor cells.

According to a further aspect of the invention, there is provided a compound of formula (I) for use in a method of increasing the number of CD34 positive, CD48 negative haematopoietic progenitor cells.

According to a further aspect of the invention, there is provided a compound of formula (I) for use in a method of increasing the number of CD48 positive haematopoietic progenitor cells.

According to a further aspect of the invention, there is provided a compound of formula (I) for use in a method of increasing the number of CD48 positive, CD150 positive haematopoietic progenitor cells.

According to a further aspect of the invention, there is provided a compound of formula (I) for use in a method of increasing the number of CD150 negative haematopoietic progenitor cells.

According to a further aspect of the invention, there is provided a compound of formula (I) for use in a method of increasing the number of CD150 negative, CD135 negative haematopoietic progenitor cells.

According to a further aspect of the invention, there is provided a compound of formula (I) for use in a method of increasing the number of CD135 positive haematopoietic progenitor cells.

According to a further aspect of the invention, there is provided a compound of formula (I) for use in a method of increasing the number of CD34 positive, CD48 positive haematopoietic progenitor cells.

According to a further aspect of the invention, there is provided a compound of formula (I) for use in a method of increasing the number of CD48 positive, CD150 negative haematopoietic progenitor cells.

Compounds of formula (I) are believed to have an effect on stem cells per se, in addition, to haematopoietic stem cells. Therefore, according to a further aspect of the invention there is provided a compound of formula (I) for use in a method of modulating stem cell function. The modulation of stem cell function includes:

(i) Promoting stem cell regeneration;
(ii) Promoting expansion in stem cell number;
(iii) Preventing, reversing or slowing stem cell ageing;
(iv) Preventing, reversing or slowing stem cell senescence; and/or
(v) Promoting stem cell differentiation.

According to a further aspect of the invention there is provided a compound of formula (I) for use in a method of expanding the number of stem cells, either in-vivo, in-vitro or ex-vivo.

According to a further aspect of the invention there is provided a compound of formula (I) for use in the ex-vivo expansion of stem cells prior to return to a patient for subsequent regeneration therapy.

According to a further aspect of the invention, there is provided a cell produced following expansion of a stem cell ex-vivo.

Examples of stem cells include, pluripotent stems cells, induced pluripotent stem cells (iPS), embryonic stem cells, and adult stem cells. Further examples of stem cells include: haematopoietic stem cells, muscle stem cells, skin stem cells, liver stem cells, neuronal stem cells, melanocyte stem cells, hair follicle stem cells, mesenchymal stem cells, adipose-derived stem cells, limbal stem cells (corneal stem cells), cardiac stem cells, intestinal stem cells, epithelial stem cells, autologous stem cells and allogeneic stem cells.

According to a further aspect of the invention there is provided a compound of formula (I) for use in a method of:
supporting stem cell regeneration;
helping optimize stem cell regeneration;
promoting stem cell regeneration;
stimulating stem cell regeneration;
supporting stem cell function;
helping optimize stem cell function; and/or
promoting stem cell function.

According to a further aspect of the invention there is provided a compound of formula (I) for use in a method of:
supporting stem cell regeneration;
helping optimize stem cell regeneration;
promoting stem cell regeneration;
boosting stem cells; and/or
increasing the number of stem cells.

According to a further aspect of the invention there is provided a compound of formula (I) for use in a method of increasing the number of stem cells. In one embodiment the number of stem cells are increased by at least about 5%, for example at least about 10%, at least about 15%, at least about 20% or at least about 25%.

Stem cells are generally in a quiescent state, arrested in the cell cycle in such a way that they can re-enter to proliferate to produce new stem cells as required and then re-enter the quiescent state until required to proliferate again. During ageing stem cells enter a senescent state where they are no longer able to re-enter the cell cycle. Support may be required to prevent stem cells entering a senescent state and thus maintain an active, healthy stem cell population. Thus, according to a further aspect of the invention there is provided a compound of formula (I) for use in a method of supporting stem cells. According to a further aspect of the invention there is provided a compound of formula (I) for use in a method of preventing and/or inhibiting stem cell senescence.

Changes that have been reported in ageing haematopoietic stem cells include reduced capacity to differentiate into lymphocytes, increased capacity to differentiate into myeloid lineages, increase in expression of the cell cycle inhibitor, $p16^{INKa}$ and reduced ability to repopulate haematopoietic stem cell progenitors. Therefore, according to a further aspect of the invention there is provided a compound of formula (I) for use in a method of treating stem cell ageing in a human or animal subject, which comprises achieving one of more of the following, improving capacity to differentiate into lymphocytes, decreasing capacity to differentiate into myeloid lineages, decreasing expression of the cell cycle inhibitor, $p16^{INKa}$ and improving ability to repopulate haematopoietic stem cell progenitors.

According to a further aspect of the invention there is provided the use of a compound of formula (I) in the manufacture of a medicament for use in a method of treating stem cell ageing in a human or animal subject, which comprises one of more of the following, improving capacity to differentiate into lymphocytes, decreasing capacity to differentiate into myeloid lineages, decreasing expression of the cell cycle inhibitor, $p16^{INKa}$ and improving ability to repopulate haematopoietic stem cell progenitors.

According to a further aspect of the invention there is provided a compound of formula (I) for use in a method of treating stem cell ageing in a human or animal subject, which comprises one of more of the following, improving capacity to differentiate into lymphocytes, decreasing capacity to differentiate into myeloid lineages, decreasing expression of the cell cycle inhibitor, p16$^{INKa}$ and improving ability to repopulate haematopoietic stem cell progenitors, which comprises the administration of an effective amount of a compound of formula (I) to a human or animal subject.

Changes observed during immunosenescence also include dysfunction in the innate immune system, impaired B cell development, thymic involution, reduced T cell output and reduced T cell diversity. Therefore, according to a further aspect of the invention there is provided a compound of formula (I) for use in a method of treating immunosenescence in a human or animal subject, wherein the treatment comprises reversing, reducing or halting changes in the innate immune system, reversing, reducing or halting impairments in B cell development, reversing, reducing or halting thymic involution, reversing, reducing or halting reductions in T cell output and reversing, reducing or halting reductions in T cell diversity.

According to a further aspect of the invention there is provided the use of a compound of formula (I) in the manufacture of a medicament for use in a method of treating immunosenescence in a human or animal subject, wherein the treatment comprises reversing, reducing or halting changes in the innate immune system, reversing, reducing or halting impairments in B cell development, reversing, reducing or halting thymic involution, reversing, reducing or halting reductions in T cell output and reversing, reducing or halting reductions in T cell diversity.

According to a further aspect of the invention there is provided a method of treating immunosenescence in a human or animal subject, wherein the treatment comprises reversing, reducing or halting changes in the innate immune system, reversing, reducing or halting impairments in B cell development, reversing, reducing or halting thymic involution, reversing, reducing or halting reductions in T cell output and reversing, reducing or halting reductions in T cell diversity, which comprises the administration of an effective amount of a compound of formula (I) to a human or animal subject.

One important role for the immune system is to fight external infections and vaccination is an important tool in this. In immunocompromised subjects and in elderly subjects, there is a general decrease in the immune response and the response to vaccination is impaired which reduces the effectiveness of vaccination and the subjects are more susceptible to flu, in general. According to another aspect of the invention, there is provided a compound of formula (I) for use in (i) raising an immune response to an antigen and/or (ii) enhancing, modulating or augmenting an immune response to an antigen in a human or animal subject, wherein the subject is an elderly or immunocompromised subject.

According to another aspect of the invention, there is provided a compound of formula (I) for use in (i) raising an immune response to an antigen and/or (ii) enhancing, modulating or augmenting an immune response to an antigen in a human or animal subject, wherein the immune response is directed to a vaccine.

An immune response comprises a number of components and a compound of formula (I) would be expected to show benefit in one or more of these components. These include:
(i) Improvements in antibody titres;
(ii) Improvements in immune cells' response, for example, in the function of CD4 T cells, CD8 T cells, dendritic cells, macrophages, natural killer (NK) cells and/or B cells and/or
(iii) Improvement in cytokine responses.

In one embodiment, improvements in antibody titres would be at least 5%, for example at least 10%, such as at least 15% or 20%, such as at least 25% or 30%.

In a further embodiment, improvements in seroconversion rates would be 5% or higher, for example 10% or higher, such as 15% or higher or 20% or higher, such 25% or higher or 30% or higher.

In another embodiment, improvements in seroprotection rates would be 5% or higher, for example 10% or higher, such as 15% or higher or 20% or higher, such as 25% or higher or 30% or higher.

In another embodiment peak antibody titres would be at least 2-fold, at least 3-fold, at least 4-fold or at least 5-fold higher.

According to a further aspect of the invention there is provided a compound of formula (I) for use in a method for increasing antibody titres in response to vaccine administration in a subject animal, comprising treating said animal with an effective amount of a compound of formula (I).

Vaccination can be against any pathogenic bacteria or pathogenic virus, which causes illness in a human or animal subject. Therefore, according to a further aspect of the invention there is provided a compound of formula (I) for use in (i) raising an immune response to an antigen and/or (ii) enhancing, modulating or augmenting an immune response to an antigen in a human or animal subject, wherein the immune response is directed to a vaccine against influenza, chicken pox, diphtheria, meningococcus, measles, mumps, pertussis, pneumococcus, polio, rubella, tetanus, tuberculosis, zika, ebola, typhoid fever and/or yellow fever.

According to a further aspect of the invention, there is provided a method of vaccination comprising:
a) administering a compound of formula (I) as an immune enhancer; and
b) administering the vaccine.

According to a further aspect of the invention, there is provided a method of vaccination comprising:
a) administering a urolithin as an immune enhancer; and
b) administering the vaccine.

For the avoidance of doubt, the compound of formula (I) and urolithin may be administered in either order with the vaccine or they can be administered concurrently.

A particularly preferred vaccine is one directed to the influenza virus. Influenza virus occurs in several types, Influenza A, Influenza B, Influenza C and Influenza D. Therefore, according to a further aspect of the invention there is provide a method or use of the invention wherein the vaccination is against Influenza A, Influenza B, Influenza C or Influenza D. In one aspect of the invention the vaccination is against influenza A. In a further aspect of the invention the vaccination is against influenza B.

Influenza A occurs as a number of variants (serotypes). In a further aspect of the invention there is provide a method or use of the invention wherein the vaccination is against Influenza A wherein the serotype is selected from H1N1, H2N2, H3N2, H5N1, H7N7, H1N2, H9N2, H7N2, H7N3, H10N7 and/or H7N9, particularly H1N1 and/or H3N2.

In one aspect of the invention, a compound of formula (I) is administered concurrently with a vaccine in a method or use of the invention. In another aspect, a compound of formula (I) is administered before the vaccine in a use or method of the invention, with administration optionally continued after vaccination. The compound of formula (I) may be administered weeks or days before the vaccine, for example, one to 12 weeks, such as one to 8 weeks or one to 4 weeks. Alternatively, the compound of formula (1) may be administered about 1 week, about 2 weeks, about 3 weeks, about 4 weeks, about 5 weeks or about 6 weeks before the administration of the vaccine.

Vaccines may be delivered to the subject in any form wherein the vaccine is able to elicit an immune response. Examples of routes of administration include: by parenteral, subcutaneous, intradermal, oral, intranasal, sublingual, via inhalation, topical, rectal, buccal, and vaginal. Therefore, according to a further aspect of the invention there is provide a method or use of the invention wherein the vaccination is administered via one or more of the following routes: parenteral, subcutaneous, intradermal, oral, intranasal, sublingual, via inhalation, topical, rectal, buccal, and vaginal.

It is believed that a compound of formula (I) when used in methods and uses of the invention will be particularly effective in elderly subjects and children. Therefore, according to a further aspect of the invention there is provided a method or use of the invention wherein the subject is a child, a senior or an elderly person.

A senior person may be above 50 years of age, for example above 55 years of age, such as above 60 years of age, for example between 50 and 65 years of age.

Elderly patients may be above 65 years of age, for example above 70 years of age, for example above 75 years of age, such as above 80 years of age, for example between 65 and 80 years of age, such as between 65 and 90 years of age, such as between 90 to 100 years of age, such as older than 100 years of age.

Children may be aged from birth to about 18 years of age, such as from birth to about 1 years, for example, from birth to about 10 years, such as from birth to 4 to 5 years.

It is also believed that a compound of formula (I) when used in methods and uses of the invention will be particularly effective in immunocompromised subjects, for example, immunocompromised subject infected with, or at risk from infection with HIV, hepatitis and tuberculosis. Therefore, according to a further aspect of the invention there is provided a method or use of the invention wherein the subject is an immunocompromised subject, for example, a subject infected by HIV, hepatitis and/or tuberculosis.

Compounds of formula (I) enhance immune responses to antigens, particularly in response to vaccination, and therefore act as immune enhancers. Compounds of formula (I) can be used with one or more additional immune enhancer components to further enhance the immune response. Therefore, according to a further aspect of the invention there is provided an immune enhancer composition comprising a compound of formula (I) and one or more additional immune enhancer components. Such compositions include compositions intended to be administered prior to vaccination and compositions wherein the compound of formula (I) is administered first and the one or more additional immune enhancer components are administered after a period of time. Administration of the immune enhancer may stop upon vaccination or be also delivered concurrently with vaccination and afterwards. The period of time may vary from a few hours to a few weeks.

Compounds of formula (I) may be administered in a treatment protocol with a vaccine, with or without one or more additional immune enhancer components. Therefore, according to a further aspect of the invention there is provided a treatment protocol comprising:
  (i) a compound of formula (I);
  (ii) a vaccine; and
  (iii) optionally one or more immune enhancer components.

According to a further aspect of the invention there is provided a treatment protocol wherein the vaccine comprises an inactivated or attenuated micro-organism or protein or peptide antigen derived therefrom. The inactivated or attenuated micro-organism is selected from an inactivated or attenuated virus or an inactive or attenuated bacteria. For the avoidance of doubt, a protein or peptide antigen may be derived from an active or unattenuated virus or bacteria.

In a treatment protocol a compound of formula (I) can be administered in a number of ways, as follows:
  Primary prevention: a compound of formula (I) is given before vaccination to prime/sensitize the immune system to be ready for vaccination; and/or
  Secondary prevention: a compound of formula (I) is given along with vaccination/immune sensitization (as an immune enhancer—for example, orally as a tablet with the sub-cutaneous vaccination in parallel) to boost the immune response; and/or
  Tertiary prevention: a compound of formula (I) is given after the vaccination/flu response has set in to mitigate or manage symptoms of the flu episodes.

According to a further aspect of the invention the vaccine is an inactivated or attenuated micro-organism or antigen selected from one or more of the following: influenza, chicken pox, diphtheria, meningococcus, measles, mumps, pertussis, pneumococcus, polio, rubella, tetanus, tuberculosis, zika, ebola, typhoid fever and/or yellow fever or a protein, subunit or peptide derived therefrom. Preferably influenza or a protein, subunit or peptide derived therefrom.

Increasing the number of functional haematopoietic stem cells is beneficial to the overall renewal of the haematopoietic system and leads to: improved immune function; a decreased incidence of bone marrow failure, for example following irradiation or following bone marrow transplantation; and is a treatment for anaemia. This can be used for the improvement of recovery from the cytotoxic effects of chemotherapy treatments used to treat cancer (such as leukaemia and lymphoma), treatment and/or prevention of myelosuppression as a result of chemotherapy treatment; and the improvement in bone marrow transplantation and reduction in transplantation related mortality. Therefore, according to a further aspect of the invention there is provided a compound of formula (I) for use in a method of increasing the number of functional haematopoietic stem cells, for example, for use:
  (i) prior to treatment of a patient and/or bone marrow harvesting in a donor;
  (ii) in treatment following irradiation and/or following bone marrow transplantation;
  (iii) in treatment of the cytotoxic effects of chemotherapy treatments; and/or
  (iv) in treatment and/or prevention of myelosuppression as a result of chemotherapy treatment.

According to a further aspect of the invention there is provided a compound of formula (I) for use:
  (i) prior to treatment of a patient and/or bone marrow harvesting in a donor
  (ii) in treatment following irradiation and/or following bone marrow transplantation;
  (iii) in treatment of the cytotoxic effects of chemotherapy treatments; and/or
  (iv) in treatment and/or prevention of myelosuppression as a result of chemotherapy treatment.

Haematopoietic stem cells are also the source of new red blood cells. Therefore, according to a further aspect of the invention there is provided a compound of formula (I) for use in the prevention and/or treatment of anaemia.

Compounds of formula (I) can also be used in patients being treated by irradiation, for example, in the treatment of cancers. Therefore, according to a further aspect of the invention there is provided the use of a compound of formula (I) as an immune enhancer during irradiation treatment in a patient. Compounds of formula (I) may be used to enhance the immune system before or during the irradiation to limit damage to the immune system during treatment. Alternatively or additionally compounds of formula (I) may be used after irradiation to enhance recovery of the immune system.

Compounds of formula (I) may be used as immune enhancers during bone marrow cell transplantation prior to harvesting of bone marrow cells for subsequent transplantation and/or after transplantation of the bone marrow cells back into the patient to enhance repopulation of the bone marrow. Compounds of formula (I), may be used, ex-vivo in the expansion of bone marrow cells prior to return to a patient following an immunosuppressive therapy, such a cytotoxic chemotherapy for the treatment of cancer.

Compounds of formula (I) may be used, ex-vivo or in vivo to increase the number and function of immune cells used for cancer immunotherapy, including natural killer cells, macrophages and activated T-cells.

Compounds of formula (I) may be used, ex vivo in the expansion of CAR-T, TCR-T or other engineered T cells (Kershaw, M. H., Westwood, J. A., & Darcy, P. K. Gene-engineered T cells for cancer therapy. Nature Reviews Cancer, 2013) prior to return to a patient for subsequent cancer immunotherapy.

Compounds of formula (I) may be used ex vivo to increase the number and function of mesenchymal stem cells prior to return to a patient for cartilage regeneration.

Compounds of formula (I) may be used to stimulate the differentiation of pluripotent stems cells, induced pluripotent stem cells (iPS), embryonic stem cells, and adult stem cells into keratinocytes prior to return to a patient for skin transplantation.

According to a further aspect of the invention there is provided a compound of formula (I) for use in a method to prevent and/or treat the cytotoxic effects of chemotherapy. According to a further aspect of the invention there is provided a compound of formula (I) for use in a method to prevent and/or treat myelosuppression for example, myelosuppression following cytotoxic chemotherapy.

Neuronal stem cell (NSC) exhaustion has been implicated to play a role in olfactory decline during ageing. Therefore, according to a further aspect there is provide a compound of formula (I) for use in method of treating olfactory decline, for example, olfactory decline during ageing.

According to a further aspect of the invention there is provided a compound of formula (I) in a method of promoting expansion of inner-ear hair progenitor cells.

Additionally, NSC's are stimulated to proliferate in response to seizures, suggesting that NSC proliferation leads to increased neurogenesis to repair brain damage or neuronal loss. Therefore, according to a further aspect of the invention there is provided a compound of formula (I) for use in a method of promoting brain repair. According to a further aspect of the invention there is provided a compound of formula (I) or use in a method of preventing, inhibiting or slowing neuronal loss. According to a further aspect of the invention there is provided a compound of formula (I) for use in a method of preventing and/or treating seizures.

Increasing the number of functional neuronal stem cells will promote neurogenesis which can support learning, for example, adaptive learning. Therefore, according to a further aspect of the invention there is provided a compound of formula (I) for use in a method of increasing neurogenesis.

According to a further aspect of the invention there is provided a compound of formula (I) for use in a method of supporting learning, for example, adaptive learning.

Decreased melanocyte stem cell function and/or decreased numbers of melanocyte stem cells has been implicated in hair greying during ageing. Therefore, according to a further aspect of the invention there is provided a compound of formula (I) in a method of preventing, inhibiting or slowing loss of hair colour or hair greying, for example, loss of hair colour or hair greying during ageing.

Decreased hair follicle stem cell function and/or decreased number of hair follicle stem cells may be involved in bodily hair loss and baldness. Therefore, according to a further aspect of the invention there is provided a compound of formula (I) for use in a method of (i) preventing, inhibiting or slowing bodily hair loss and/or baldness; (ii) promoting and/or improving hair growth; and/or (iii) promoting and/or improving hair growth following transplantation.

According to a further aspect of the invention, there is provided a compound of formula (I) for use in a method of hair follicle stem cell regeneration, and/or increasing the hair stem cell renewal rate.

According to a further aspect of the invention there is provided a compound of formula (I) for use in a method of hair follicle stem cell differentiation.

According to a further aspect of the invention, there is provided a compound of formula (I) for use in a method of increasing hair growth. The rate of hair growth can be measured by the rate of formation of a hair shaft, or the rate of formation of hair follicles having activity to form a hair shaft. In some embodiments, the effects can include changes in the thickness of the hair shaft.

According to a further aspect of the invention, there is provided a compound of formula (I) for use in a method of increasing hair follicle number. In one embodiment the compound of formula (I) promote at least a 5%, 10%, 15%, 20%, 25% increase in hair follicle number (or follicular units) over a period of several weeks to several months. For example, at least a 10% increase in hair follicle number (or follicular units) over a period of several weeks to several months. For example, a 50% (or more) increase in hair follicle number (or follicular units) over a period of several weeks to several months.

According to a further aspect of the invention there is provided a compound of formula (I) for decreasing hair loss. In one embodiment there is at least a 5%, 10%, 15%, 20%, 25% decrease in hair loss over a period of several weeks to several months. For example, at least a 10% decrease in hair loss over a period of several weeks to several months. For example, a 50% (or more) decrease in hair loss over a period of several weeks to several months.

According to a further aspect of the invention there is provided a compound of formula (I) for use in a medical conditions that would benefit from an increase in hair follicle stem cell growth and/or hair growth, for example, alopecia areata, androgenic alopecia, male pattern baldness and chemotherapy induced alopecia.

According to a further aspect of the invention, there is provided a compound of formula (I) for use in a method of treating male pattern baldness.

According to a further aspect of the invention, there is provided a compound of formula (I) for use in a method of treating alopecia.

According to a further aspect of the invention there is provided a compound of formula (I) for improving existing hair. Improving existing hair includes increasing hair thickness.

According to a further aspect of the invention there is provided a composition for (i) preventing, inhibiting or slowing of bodily hair loss and/or baldness; (ii) promoting and/or improving hair growth; and/or (iii) promoting and/or improving hair growth following transplantation comprising a compound of formula (I) characterised is that the composition is a tonic, a lotion, a serum, a shampoo, a conditioner, a spray, a gel or a cream. In a further embodiment the compound of formula (I) or salt thereof is present in the composition at a concentration in the range of from 0.01 µM to 100 mM, from 0.01 µM to 10 mM, from 0.01 µM to 1 mM, from 0.01 µM to 100 µM, from 0.1 µM to 500 µM, from 0.1 µM to 100 µM, or from 1 µM to 50 µM.

A decreased renewal rate of beta-cells in the pancreatic islets increases the possibility of type 2 diabetes during ageing. Therefore, according to a further aspect of the invention, there is provided a compound of formula (I) for use in a method of preventing, inhibiting, slowing and/or reversing the decrease in renewal rates of beta cells in pancreatic islets. According to a further aspect of the invention there is provided a compound of formula (I) for use increasing the renewal rate of beta cells in the pancreatic islets.

A decreased in the number and function of muscle stem cells leads to a decrease in muscle regenerative capacity after injury. Therefore, according to a further aspect of the invention there is provided a compound of formula (I) for use in a method of increasing the number of muscle stem cells.

According to a further aspect of the invention there is provided a compound of formula (I) for use in a method of promoting muscle regenerative capacity.

According to a further aspect of the invention there is provided a compound of formula (I) for use in a method of promoting muscle stem cell regenerative capacity.

According to a further aspect of the invention there is provided a compound of formula (I) for use in a method of promoting and/or improving muscle regeneration, for example, following injury or surgery.

According to a further aspect of the invention there is provided a compound of formula (I) for use in a method of promoting and/or improving muscle regeneration, for example following injury or surgery, in a senior or elderly patient.

According to a further aspect of the invention there is provided a compound of formula (I) for use in a method of promoting and/or improving muscle regeneration following exercise.

According to a further aspect of the invention there is provided a compound of formula (I) for use in a method of increasing muscle stem cell number.

Effects on muscle stem cells can be identified by FACS (fluorescence activated cell sorting).

Two examples of ways to select muscle stem cell populations, and observe the beneficial impact of this invention of muscle stem cells is to employ the use of the following combination of markers:
 1. CD31 negative, CD45 negative, SCA negative, VCAM positive muscle stem cells
 2. CD31 negative, CD45 negative, CD11b negative, SCA negative, Integrin a7 positive, CD34 positive muscle stem cells.

According to a further aspect of the invention, there is provided a compound of formula (I) for use in a method of increasing the number of CD31 negative, CD45 negative, SCA negative, VCAM positive muscle stem cells.

According to a further aspect of the invention, there is provided a compound of formula (I) for use in a method of increasing the number of CD31 negative, CD45 negative, CD11b negative, SCA negative, Integrin a7 positive, CD34 positive muscle stem cells.

According to a further aspect of the invention there is provided a compound of formula (I) for use in a method of promoting muscle regeneration after injury. According to a further aspect of the invention there is provided a compound of formula (I) for use in a method of increasing muscle regenerative capacity. According to a further aspect of the invention there is provided a compound of formula (I) for use in a method of muscle healing following injury. Compounds of formula (I) may be used, ex-vivo in the expansion of muscle stem cells prior to return to a patient for subsequent muscle regeneration therapy. Therefore, according to a further aspect of the invention there is provided a compound of formula (I) for use in a method of muscle stem cell expansion, for example, an ex-vivo method of muscle stem cell expansion.

Compounds of formula (I) are also believed to have a role in the differentiation of stem cells to more mature phenotypes such as progenitor cells and terminally differentiated cells, such as muscle cells, hair cells, haematopoietic cells and neural cells. Without being bound by theoretical principles this is believed to be by acting as an accessory factor to other differentiation inducing factors.

Therefore, according to a further aspect of the invention there is provided a compound of formula (I) for use in a method of inducing stem cell, for example pluripotent stem cell, differentiation. According to a further aspect of the invention there is provided a compound of formula (I) for use in a method of inducing progenitor cell differentiation.

Examples of cells wherein compounds of formula (I) promote differentiation include, pluripotent stems cells, induced pluripotent stem cells (iPS), embryonic stem cells, and adult stem cells.

Further examples of cells include: haematopoietic stem cells, muscle stem cells, skin stem cells, liver stem cells, neuronal stem cells, melanocyte stem cells, hair follicle stem cells, mesenchymal stem cells, adipose-derived stem cells, limbal stem cells (corneal stem cells), cardiac stem cells, intestinal stem cells, epithelial stem cells, autologous stem cells and allogeneic stem cells.

According to a further aspect of the invention, there is provided a composition comprising:
 a) a compound of formula (I); and
 b) one or more differentiation-inducing factors.

Examples of differentiation-inducing factors include: growth differentiation factors, retinoids, such as retinoic acid, butyrate such as sodium butyrate, activin, fibroblast growth factors (such as basic FGF), transforming growth factors (such as TGF-β), myostatin, insulin growth factor 1, vascular endothelial growth factor A, bone morphogenetic proteins, interleukin 3, interleukin 6, stem cell factor, epidermal growth factor, colony simulating factors (such as GM-CSF and M-CSF) and glucagon-like peptide type 1.

Friedreich's ataxia is an autosomal recessive disorder that affects a gene (FXN) on chromosome 9 which produces an important protein called frataxin. Frataxin has a role in mitochondria and it is believed a compound of formula (I) has a role in alleviating the effects of this biochemical lesion.

According to a further aspect of the invention there is provided a compound of formula (I) for the treatment of Friedreich's ataxia.

According to a further aspect of the invention there is provided a compound of formula (I) for use in a method of the invention in a patient or subject in need thereof.

DETAILED DESCRIPTION OF THE INVENTION

Figure 1A:
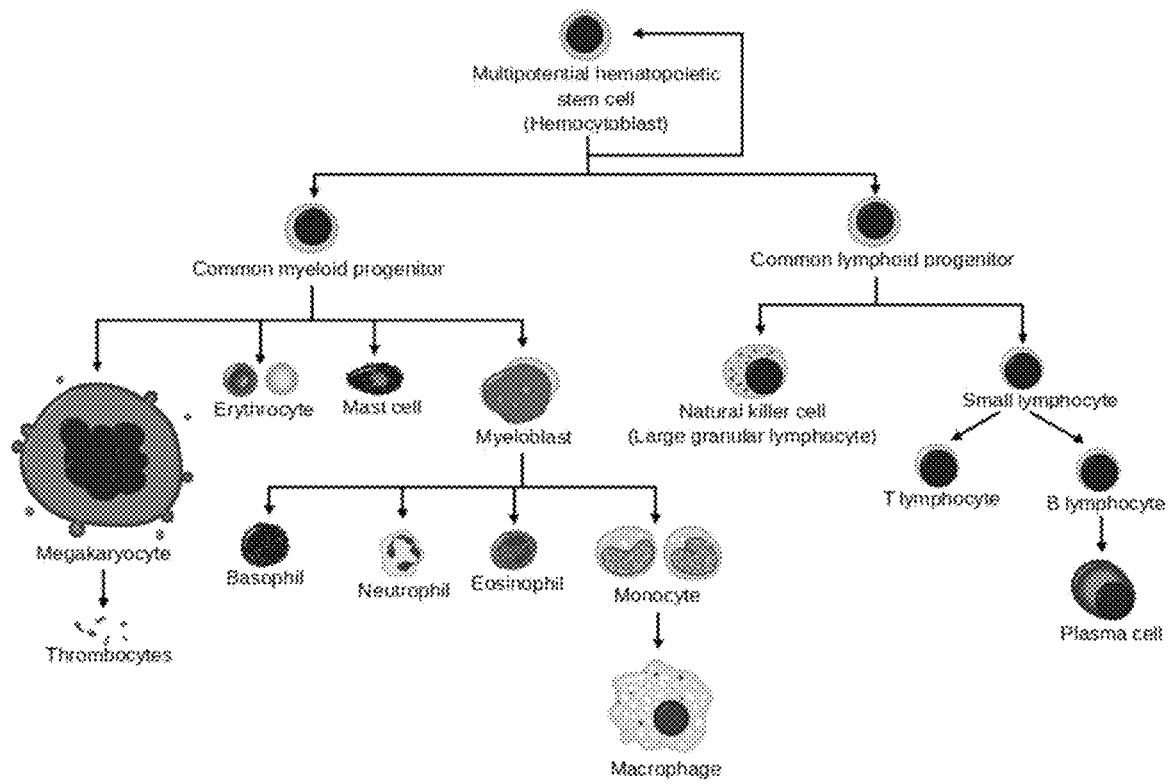
FIG. 1A shows the different blood cellular lineages derived from the haematopoietic stem cell.

The term 'about' refers to a tolerance of ±20% of the relevant value, for example ±15% of the relevant value, such as ±10% of the relevant value or ±5% of the relevant value.

The term 'immune enhancer' refers to any substance that acts to accelerate, prolong, or enhance antigen-specific immune responses when used in combination with specific vaccine antigens and/or any substance which improves immune health such that an individual is better able to mount an immune response against an infection or cancer.

The term 'antigen' refers to a protein, sub-unit, peptide or other compound which when recognized as non-self by a subject triggers an immune response. Such an immune response may be via innate and/or adaptive mechanisms to mobilize a response to an invading pathogen, toxin or allergen. An antigen may generally be derived from a pathogenic organism, such as a pathogenic bacteria or pathogenic virus. An antigen may also be derived from a malignant cell.

The term 'immune cell' refers to any cell involved in a subject's defenses to infection by microorganisms such as bacteria and viruses. The term also relates to any cell involved in a subject's defenses to cancer cells. Immune cells include: phagocytic cells such as neutrophils and macrophages, cytotoxic natural killer (NK) cells, and granulocytes, macrophages, dendritic cells, T cell subsets including memory cells, B cells, and macrophages.

The term 'inflammageing' refers to the chronic low grade inflammation that accompanies the aging process.

The term 'immunodeficiency' refers to a state in which the immune system's ability to fight infectious disease and/or cancer is compromised or entirely absent. A person who has an immunodeficiency of any kind is said to be immunocompromised.

The term 'immunosenescence' refers to the gradual deterioration of the immune system brought on by natural age advancement. It refers to both the host's capacity to respond to infections and the development of long-term immune memory, especially by vaccination.

The term 'salt' refers to any pharmaceutically acceptable salt or non-pharmaceutically acceptable salt. Whilst only pharmaceutically acceptable salts would be suitable for administration to subjects, non-pharmaceutically acceptable salts may be used as intermediates in the formation of pharmaceutically acceptable salts.

The term 'seroconversion, as used herein, refers to the increase in an individual, in the amount of serum antibodies directed against an immunogen which the individual has been vaccinated with, subsequent to vaccination the post vaccination antibody level, for example, being at least equal to 2 times to at least 4 times the antibody level measured before vaccination, for example, post vaccination for the common flu strains (H1N1, H3N2, Type B).

The term 'seroprotection' as used herein refers to the presence of antibodies in an individual of serum antibodies directed against an immunogen, which the individual has been vaccinated with, in an amount greater than or equal to a protection threshold that confers protection against an infectious agent.

The term stem cell senescence refers to a stable and irreversible (without therapeutic intervention) loss of proliferative capacity despite continued viability and metabolic activity.

The term 'subject', as used herein, refers to an individual, e.g., a human, cow, cat, dog, donkey, pig, horse, mouse, rat etc. having or at risk of having a disease, particularly a human. The subject may be a patient in need of treatment in accordance with the invention. The term 'subject' may include non-mammalian subjects such as reptiles.

The term 'thymic involution' refers to the shrinking of the thymus with age, resulting in changes in the architecture of the thymus and a decrease in tissue mass.

The term 'vaccine', as used herein, refers to an immunogenic composition for in-vivo administration to an animal or human subject to confer protection against a disease, particularly a viral or bacterial disease. The term 'vaccine' also refers to anti-cancer vaccines.

The present disclosure provides compositions and methods involving administration of compounds of formula (I), i.e., urolithins, such as urolithin A, which provide beneficial health effects.

Compounds of Formula (I) and Salts Thereof

Urolithins are metabolites produced by the action of mammalian, including human, gut microbiota on ellagitannins and ellagic acid. Ellagitannins and ellagic acid are compounds commonly found in foods such as pomegranates, nuts and berries. Ellagitannins are minimally absorbed in the gut themselves. Urolithins are a class of compounds with the representative structure (I) shown above. The structures of some particularly common urolithins are described in Table 1 below, with reference to structure (I).

TABLE 1

| | Substituent of structure (I) | | | | | |
|---|---|---|---|---|---|---|
| | A | B | C | D | W, X and Y | Z |
| Urolithin A | H | H | H | OH | H | OH |
| Urolithin B | H | H | H | H | H | OH |
| Urolithin C | H | H | OH | OH | H | OH |
| Urolithin D | OH | H | OH | OH | H | OH |
| Urolithin E | OH | OH | H | OH | H | OH |
| Isourolithin A | H | H | OH | H | H | OH |
| Isourolithin B | H | H | OH | H | H | H |
| Urolithin M-5 | OH | OH | OH | OH | H | OH |
| Urolithin M-6 | H | OH | OH | OH | H | OH |
| Urolithin M-7 | H | OH | H | OH | H | OH |

In practice, for commercial scale products, it is convenient to synthesise the urolithins. Routes of synthesis are described, for example, in WO 2014/004902 and WO 2015/100213.

Urolithins of any structure according to structure (I) may be used in the methods of the present disclosure.

In one aspect of the uses and methods of the present disclosure, a suitable compound is a compound of formula (I) wherein A, C, D and Z are independently selected from H and OH and B, W, X and Y are all H, preferably at least one of A, C, D and Z is OH.

Particularly suitable compounds are the naturally-occurring urolithins. Thus, Z is preferably OH and W, X and Y are preferably all H. When W, X and Y are all H, and A, and B are both H, and C, D and Z are all OH, then the compound is Urolithin C. When W, X and Y are all H, and A, B and C are all H, and D and Z are both OH, then the compound is urolithin A. Preferably, the urolithin used in the methods of the present disclosure is urolithin A, urolithin B, urolithin C or urolithin D. Most preferably, the urolithin used is urolithin A.

According to one embodiment there is provided a method of the invention wherein the compound of formula (I) is urolithin A.

According to one embodiment there is provided a method of the invention wherein the compound of formula (I) is urolithin B.

According to one embodiment there is provided a method of the invention wherein the compound of formula (I) is urolithin C.

According to one embodiment there is provided a method of the invention wherein the compound of formula (I) is urolithin D.

Urolithin A

The term pharmaceutically acceptable salt as applied to compounds of formula (I) defines any non-toxic organic or inorganic acid addition salt of the free base compounds which are suitable for use in contact with the tissues of humans and lower animals without undue toxicity, irritation, allergic response and which are commensurate with a reasonable benefit/risk ratio. Suitable salts according to the invention include those formed with organic or inorganic bases.

Pharmaceutically acceptable base salts include ammonium salts, alkali metal salts, for example those of potassium and sodium, alkaline earth metal salts, for example those of calcium and magnesium, and salts with organic bases, for example dicyclohexylamine, N-methyl-D-glucomine, morpholine, thiomorpholine, piperidine, pyrrolidine, a mono-, di- or tri-lower alkylamine, for example ethyl-, tert-butyl-, diethyl-, diisopropyl-, triethyl-, tributyl- or dimethyl-propylamine, or a mono-, di- or trihydroxy lower alkylamine, for example mono-, di- or triethanolamine.

These salts can exist in either a hydrated or a substantially anhydrous form. Crystalline forms of the compounds of formula (I) are also contemplated for use in uses or methods of the invention.

Administration/Dosage Regimes

The methods of the present disclosure involve oral administration of a compound of formula (I) or salt thereof to a subject in a daily amount in the range of 1.7 to 6.0 mmol per day, for a period between 2 to 16 weeks prior to vaccination, for example, from 1.7 to 2.7 mmol per day, for a period between 2 to 16 weeks prior to vaccination or from 2.8 to 6.0 mmol per day, for a period between 2 to 16 weeks prior to vaccination. As discussed below, administration of is preferred in the range 250 mg to 1000 mg urolithin A (which corresponds to about 1.1 to 4.4 mmol) results in a surprisingly good pharmacokinetic profile, compared with a much higher dosage of 2000 mg. In one embodiment the dose is 250 mg/day, in an alternative embodiment the dose is 500 mg/day and in another embodiment the dose is 1000 mg/day.

In a further embodiment, administration doses are selected from:
  250 mg once or twice a day;
  500 mg once or twice a day;
  750 mg once or twice a day;
  1000 mg once or twice a day;
  1250 mg once or twice a day; or
  1500 mg once or twice a day The methods of the present disclosure involve daily administration of the compound of formula (I) or salt thereof, or of a composition containing the compound or salt. In some embodiments, the compound or composition is administered once per day, i.e., the compound or composition is to be administered at least once per 24 hour period. In other embodiments, the compound, or composition comprising the compound, is administered multiple times per day, for example twice per day, or three or four times per day. In such cases, the daily dosage is divided between those multiple doses. In one embodiment administration is once a day, in a second embodiment administration is twice a day, in a third embodiment administration is three times a day.

The methods of the present disclosure require daily administration of the compound of formula (I) or salt thereof, or of a composition containing the compound or salt, for a period between 2 to 16 weeks. In some embodiments, the methods may involve administration of the compound of formula (I), or salt thereof, over a still longer period of time, for example daily for at least 2 weeks, 3 weeks, 4 weeks, 5 weeks, 6 weeks, 8 weeks, 12 weeks, 4 months, 6 months, or for at least a year. In some embodiments, the method comprises administering the compound or salt thereof daily for a period of up to 3 months, up to 6 months, up to 1 year, up to 2 years or up to 5 years. In some embodiments, the method comprises administering the compound or salt daily for a period in the range of from 21 days to 5 years, from 21 days to 2 years, from 21 days to 1 year, from 21 days to 6 months, from 21 days to 12 weeks, from 28 days to 5 years, from 28 days to 2 years, from 28 days to 1 year, from 28 days to 6 months, from 28 days to 4 months, from 28 days to 12 weeks, 6 weeks to 2 years, from 6 weeks to 1 year, from 8 weeks to 1 year, or from 8 weeks to 6 months.

The methods of the present disclosure require daily administration of an amount of compound of formula (I) or salt thereof, of from 0.7 mmol per day up to 2.7 mmol per day thereof or from 0.7 mmol twice per day up to 2.7 mmol twice a day. In some embodiments, the amount administered is in the range of from 2.0 to 2.5 mmol. In some embodiments, the amount administered is approximately, 1.1, 1.2, 1.3, 1.4. 1.5, 1.6 1.7, 1.8, 1.9, 2.0, 2.1, 2.2, 2.3, 2.4, 2.5, 2.6, or 2.7 mmol. In other embodiments, the amount administered is approximately, 2.8, 2.9, 3.0, 3.1, 3.2, 3.3, 3.4, 3.5, 3.6, 3.7, 3.8, 3.9, 4.0, 4.1, 4.2, 4.3, 4.4, 4.5, 4.6, 4.7, 4.8, 4.9, 5.0, 5.1, 5.2, 5.3, 5.4, 5.5, 5.6, 5.7, 5.8, 5.9, or 6.0 mmol. In some preferred embodiments, the method involves administration of approximately 2.2 mmol per day or 2.2 mmol twice per day of the compound of formula (I) or salt thereof (e.g., of urolithin A). The exact weight of compound that is administered depends on the molecular weight of the compound that is used. For example, urolithin A has a molecular weight of 228 g/mol (such that 2.20 mmol is 501.6 mg) and urolithin B has a molecular weight of 212 g/mol (such that 2.20 mmol is 466.4 mg).

In a further embodiment, the methods of the present disclosure require daily administration of an amount of compound of formula (I) or salt thereof, of from 2.8 mmol per day up to 6.0 mmol per day or twice per day thereof. In some embodiments, the amount administered is in the range of from 4.0 to 4.8 mmol. In some embodiments, the amount administered is approximately, 2.8, 2.9, 3.0, 3.1, 3.2, 3.3, 3.4, 3.5, 3.6, 3.7, 3.8, 3.9, 4.0, 4.1, 4.2, 4.3, 4.4, 4.5, 4.6, 4.7, 4.8, 4.9, 5.0, 5.1, 5.2, 5.3, 5.4, 5.5, 5.6, 5.7, 5.8, 5.9, or 6.0 mmol. In some preferred embodiments, the method involves administration of approximately 4.4 mmol per day or twice per day of the compound of formula (I) or salt thereof (e.g., of urolithin A). The exact weight of compound that is administered depends on the molecular weight of the compound that is used. For example, urolithin A has a molecular weight of 228 g/mol (such that 4.40 mmol is 1003.2 mg) and urolithin B has a molecular weight of 212 g/mol (such that 4.40 mmol is 932.8 mg).

In some embodiments, the methods involve administration of urolithin A in an amount in the range of from 400 to 600 mg/day or 400 to 600 mg twice per day. In a preferred embodiment the method involves administration of urolithin A in an amount in the range of from 450 to 550 mg, more preferably approximately 500 mg per day or twice per day.

In other embodiments, the methods involve administration of urolithin A in an amount in the range of from 700 to 1300 mg/day twice per day, or in the range of from 750 to 1250 mg, or in the range of from 800 to 1200 mg, or in the range of from 850 to 1150 mg, or in the range of from 900 to 1100 mg per day or twice per day. In a preferred embodiment the method involves administration of urolithin A in an amount in the range of from 950 to 1150 mg/day or twice per day, more preferably approximately 1000 mg/day or twice per day.

In some preferred embodiments, the methods involve administering urolithin A to the subject in an amount in the range of from 4.5 to 11 mg/kg/day, such as 4.5 to 8.5 mg/kg/day. In another embodiment, the methods involve administering urolithin A to the subject in an amount in the range of 5 to 9 mg/kg/day. In another embodiment, the methods involve administering urolithin A to the subject in an amount in the range of from 6.0 to 8 mg/kg/day.

In other preferred embodiments, the methods involve administering urolithin A to the subject in an amount in the range of from 9 to 18 mg/kg/day such as 9 to 17 mg/kg/day. In another embodiment, the methods involve administering urolithin A to the subject in an amount in the range of from 10 to 17 mg/kg/day. In another embodiment, the methods involve administering urolithin A to the subject in an amount in the range of from 11 to 16 mg/kg/day.

Dosage regimes which combine a 500 mg dose and a 1000 mg dose may be advantageous. For example, a twice daily dosage regime which combines a first dose of 1000 mg and a second dose several hours later of 500 mg. Said 500 mg dose may be 6-18 hours after the 1000 mg dose, for example 8-12 hours after the 1000 mg dose. For example, about 12 hours after the 1000 mg dose. Thus, according to a further aspect of the invention there is provided the treatment of a disease with a compound of Formula (I) which comprises a twice daily dosage regime comprising a first dose of 1000 mg, followed by a second dose of 500 mg wherein the two doses are separated by 6-18 hours.

The compound of formula (I) or salt thereof, or composition containing the compound of salt, may be administered at any suitable time, for example it may be administered in the morning after sleep or in the evening. In some embodiments, it may be preferable for the method to be performed at approximately the same time(s) each day, for example within 15, 30, 60 or 120 minutes of a given time point.

Immune Enhancers

An immune enhancer is any compound or composition that increases the strength and/or duration of an immune response to a foreign antigen relative to that elicited by the antigen alone. Key functional characteristics of an immune enhancer therefore include its ability to enhance an appropriate immune response to the target antigen, long-term safety in widespread application, and flexibility in use with different antigen/disease applications.

Compounds of formula (I) can be administered with one or more additional immune enhancers.

In a further alternative embodiment of the invention said immune enhancer is a TLR agonist such as CpG oligonucleotides, flagellin, monophosphoryl lipid A, poly I:C and derivatives thereof.

In a further embodiment of the invention said immune enhancer is a bacterial cell wall derivative such as muramyl dipeptide (MDP) and/or trehalose dycorynemycolate (TDM).

In another embodiment of the invention said immune enhancer is an aluminum based immune enhancer suitable for use in a human subject.

Immune enhancers (immune potentiators or immunomodulators) have long been used to improve the immune response to vaccine antigens. The incorporation of immune enhancers into vaccine formulations is aimed at enhancing, accelerating and prolonging the specific immune response to vaccine antigens. Advantages of immune enhancers include the enhancement of the immunogenicity of weaker antigens, the reduction of the antigen amount needed for a successful immunisation, the reduction of the frequency of booster immunisations needed and an improved immune response in elderly and immunocompromised vaccines. Selectively, immune enhancers can also be employed to optimise a desired immune response, e.g., with respect to immunoglobulin classes and induction of cytotoxic or helper T lymphocyte responses. In addition, certain immune enhancers can be used to promote antibody responses at mucosal surfaces. Aluminium hydroxide and aluminium or calcium phosphate has been used routinely in human vaccines. More recently, antigens incorporated into IRIV's (immunostimulating reconstituted influenza virosomes) and vaccines containing the emulsion-based immune enhancer MF59 have been licensed in countries. Immune enhancers can be classified according to their source, mechanism of action and physical or chemical properties. The most commonly described immune enhancer classes are gel-type, microbial, oil-emulsion and emulsifier-based, particulate, synthetic and cytokines. More than one immune enhancer may be present in the final vaccine product. They may be combined together with a single antigen or all antigens present in the vaccine, or each immune enhancer may be combined with one particular antigen. The origin and nature of the immune enhancers currently being used or developed is highly diverse. For example, aluminium based immune enhancers consist of simple inorganic compounds, PLG is a polymeric carbohydrate, virosomes can be derived from disparate viral particles, MDP is derived from bacterial cell walls; saponins are of plant origin e.g., QS-21, squalene is derived from shark liver and recombinant endogenous immunomodulators are derived from recombinant bacterial, yeast or mammalian cells. There are several immune enhancers licensed for veterinary vaccines, such as mineral oil emulsions that are too reactive for human use. Similarly, complete Freund's immune enhancer, although being one of the most powerful immune enhancers known, is not suitable for human use.

Compositions

The methods of the present disclosure preferably involve oral administration of the compound of formula (I) or a salt thereof. Any suitable oral composition containing the compound of formula (I) or salt thereof may be used. Accordingly, the use of a range of compositions which contain the compound of formula (I), and which are suitable for oral administration, is envisaged. Thus in some embodiments, the compound of formula (I), or salt thereof, is administered in the form of an oral composition containing the compound of formula (I) or salt thereof and one or more excipients suitable for oral administration. Oral compositions may comprise compositions having the form of a pill, tablet, capsule, caplet, lozenge, pastille, granules, powder for suspension, oral solution, oral suspension, oral emulsion, syrup, or the like.

Compositions containing the compound of formula (I) may take any physical form suitable for the intended application, for example, they may be in the form of a solid (for example a bar), a semi-solid (for example a softgel), or a liquid (including emulsions). In some instances, the composition may be in the form of a viscous fluid or a paste. Where the composition is a bar, for example, it may be of any suitable type and it may contain ingredients conventionally used for the preparation of snack bars. Semi-solid forms may likewise contain excipients conventional in the art. The excipients can, for example, provide a desired hardness, shelf-life and flavour such that the composition has an acceptable taste, an attractive appearance and good storage stability. Semi-solid forms can be in the form of a paste. Where the composition is a softgel, it may for example be provided in a capsule having a shell. The shell may be of a conventional type, for example it may be a soft gelatin-based shell. By way of example, the composition may also be provided inside a hard capsule type of shell. Liquid compositions may be in the form of a medicine, a dietary supplement, or a beverage, each for oral consumption. Liquid formulations may be solutions, emulsions, slurries or other semi-liquids. Excipients in a liquid composition can, for example, provide a shelf-life, visual appearance, flavour and mouthfeel such that the composition has an acceptable taste, an attractive appearance and good storage stability. At certain levels of dilution, a drink may need to be shaken before the subject drinks it, so as to maintain an even suspension of the active ingredient.

In some preferred embodiments, the method comprises administration of a compound of formula (I) or salt thereof (e.g., urolithin A), in micronized form. Micronization enables the compound of formula (I) to disperse or dissolve more rapidly. Micronisation can be achieved by methods established in the art, for example compressive force milling, hamermilling, universal or pin milling, or jet milling (for example spiral jet milling or fluidised-bed jet milling) may be used. Jet milling is especially suitable. If micronized compound is used, then preferably the compound has a $D_{50}$ size of under 100 μm—that is to say that 50% of the compound by mass has a particle diameter size of under 100 μm. More preferably, the compound has a D50 size of under 75 μm, for example under 50 μm, for example under 25 μm, for example under 20 μm, for example under 10 μm. More preferably, the compound has a $D_{50}$ in the range 0.5-50 μm, for example 0.5 to 20 μm, for example 0.5 to 10 μm, for example 1.0 to 10 μm, for example 1.5 to 7.5 μm, for example 2.8 to 5.5 μm. Preferably, the compound has a $D_{90}$ size of under 100 μm. More preferably, the compound has a $D_{90}$ size of under 75 μm, for example under 50 μm, for example under 25 μm, for example under 20 μm, for example under 15 μm. The compound preferably has a $D_{90}$ in the range 5 to 100 μm, for example 5 to 50 μm, for example 5 to 20 μm, for example 7.5 to 15 μm, for example 8.2 to 16.0 μm. Preferably, the compound has a $D_{10}$ in the range 0.5-1.0 μm. Preferably, the compound of formula (I) or salt thereof (e.g., urolithin A) has a $D_{90}$ in the range 8.2 to 16.0 μm, a $D_{50}$ in the range 2.8 to 5.5 μm and a $D_{10}$ in the range 0.5 to 1.0 μm.

In a further embodiment, the compound of formula (I) or salt thereof has a size distribution selected from one of the following:

(i) $D_{50}$ size in the range 0.5 to 50 μm and a $D_{90}$ size in the range 5 to 100 μm, (ii) the compound has a $D_{90}$ size in the range 8.2 to 16.0 μm, a $D_{50}$ size in the range 2.8 to 5.5 μm and a $D_{10}$ size in the range 0.5 to 1.0 μm;

(iii) the compound of Formula (I) has a $D_{50}$ size in the range 0.5 to 20 μm and a $D_{90}$ size in the range 5 to 50 μm;

(iv) the compound of Formula (I) has a $D_{50}$ size under 50 µm and a $D_{90}$ size under 75 µm;
(v) the compound of Formula (I) has a $D_{50}$ size under 25 µm and a $D_{90}$ size under 50 µm;
(iv) the compound of Formula (I) has a $D_{50}$ size under 10 µm and a $D_{90}$ size under 20 µm;
(v) the compound of Formula (I) has a $D_{50}$ size under 10 µm and a $D_{90}$ size under 15 µm; or
(vi) the compound of Formula (I) has a $D_{50}$ size of 10 µm and a $D_{90}$ size of 20 µm.

Compositions Comprising the Compound of Formula (I) or Salt Thereof and a Medium Chain Triglyceride In some preferred embodiments, the compound of formula (I) or salt thereof (e.g., urolithin A) is administered in the form of a composition comprising: a) a medium-chain triglyceride; and b) the compound of formula (I) or salt thereof. Within those embodiments, preferably the compound of formula (I) (e.g., urolithin A) is in micronized form.

By selecting suitable medium chain triglycerides and excipients, the physical form of the composition can be tailored to the requirements of the product in question. For example, in some embodiments, the compositions may be pharmaceutical compositions. In some embodiments, the compositions may be nutritional compositions.

In many cases, compositions containing a compound of formula (I) and a medium chain triglyceride have the consistency of a viscous liquid or paste, and can be provided as a single serving supplement to a subject's general diet (for example in a bar, gel, or a softgel capsule, hard capsule, or diluted in a drink); alternatively, it can be provided as a part of or the whole of a meal.

Where the methods of the disclosure involve use of a composition comprising a medium-chain triglyceride, the medium-chain triglyceride typically makes up at least 1% w/w of the composition, for example at least 5% w/w, for example at least 10% w/w, for example at least 15% w/w. The medium-chain triglyceride preferably makes up 20% w/w or more of the composition, for example 25% w/w or more by weight, for example 30% w/w or more by weight of the composition. For example the medium-chain triglyceride may make up 1-40% w/w of the composition, 2-40% w/w of the composition, 5-40% w/w of the composition; 10-40% w/w of the composition; 1-99% w/w of the composition, 5-99% w/w of the composition, 10-99% w/w of the composition, 20-99% w/w of the composition, 5-90% w/w of the composition, 10-90% w/w of the composition, for example 20-90% w/w of the composition, 20-80% w/w of the composition for example, 30-80% w/w of the composition, for example 30-70% w/w of the composition, for example 30-60% w/w of the composition, for example 30-50% w/w of the composition, for example 30-40% w/w of the composition, for example 30-35% w/w of the composition. For example the medium-chain triglyceride may make up 40-70% w/w of the composition, for example 50-70% w/w of the composition, for example, 55-65% w/w of the composition.

In such compositions, the compound of formula (I) typically makes up from 0.1 to 80% w/w of the composition, for example 0.1 to 60% w/w, for example 0.25 to 50% w/w. For example the compound of formula (I) may make up 0.5-50% w/w of the composition. If the composition is provided as a part or the whole of a meal then the compound of formula (I) may for example make up 0.25-5% w/w of the composition, for example, 0.3-3% w/w of the composition. If the composition is provided as a single serving supplement to a subject's general diet, then the urolithin typically makes up from 20 to 80% w/w of the composition, for example 20 to 40% w/w, for example 25 to 35% w/w of the composition. For example the urolithin may make up 26-34% w/w of the composition, for example, 28-33% w/w of the composition; for example, 29-32% w/w of the composition, for example 29-31% w/w of the composition.

In such compositions, the weight ratio of the medium-chain triglyceride component to the compound of formula (I) is generally in the range 0.01:1 to 100:1, for example 0.5:1 to 100:1, for example 0.5:1 to 50:1, for example 0.5:1 to 5:1; or, for example, 1:1 to 75:1, for example 1:1 to 50:1, for example 1:1 to 20:1, for example 1:1 to 10:1, for example 1:1 to 2.5:1, for example 1:1 to 2:1, for example 1:1 to 1.5:1. The weight ratio may be in the ratio 0.01:1 to 10:1, for example 0.1:1 to 10:1 or 0.01:1 to 5:1, for example 0.01:1 to 0.1:1.

In some preferred embodiments, the method of the present disclosure involves administration of a softgel capsule comprising a filling, which filling comprises the compound of formula (I) or salt thereof (e.g., urolithin A) and one or more medium-chain triglycerides. Within those embodiments, preferably the compound of formula (I) or salt thereof (e.g., urolithin A) is micronized. In embodiments where a softgel capsule is used, the shell component may be produced using conventional ingredients.

Medium-chain triglycerides are compounds of formula $CH_2(OR^1)$—$CH(OR^2)$—$CH_2(OR^3)$ where $R^1$, $R^2$ and $R^3$ are medium chain fatty acid groups, generally of formula —$C(=O)(CH_2)_nCH_3$ where n is in the range 4 to 10, for example 6 to 8. Medium-chain fatty acids are fatty acids which have an aliphatic tail of 6-12 carbon atoms. The aliphatic tail is predominantly saturated. Particular medium-chain fatty acids include caproic acid (hexanoic acid, C6:0), caprylic acid (octanoic acid, C8:0), capric acid (decanoic acid, C10:0) and lauric acid (dodecanoic acid, C12:0). Myristic acid (tetradecanoic acid, C14:0) can also be present in minor amounts. Medium-chain triglycerides most commonly used generally have a mixture of triglycerides of caprylic acid and capric acid, and contain 95% or greater of saturated fatty acids. The medium chain triglyceride component present in preferred compositions used in the methods of the present disclosure may consist of a homogeneous, single medium chain triglyeride compound type; more commonly, the medium chain triglyceride component is a mixture of two or more different medium chain triglyeride compounds.

The European Pharmacopoeia describes medium-chain triglycerides as the fixed oil extracted from the hard, dried fraction of the endosperm of *Cocos nucifera* L. (coconut) or from the dried endosperm of *Elaeis guineenis* Jacq. (African oil palm). The European Pharmacopoeia and the USPNF both have specifications for medium-chain triglycerides that require the presence of particular fatty acids is as follows: caproic acid (C6)≤2.0%; caprylic acid (C8) 50.0-80.0%; capric acid (C10) 20.0-50.0%; lauric acid (C12)≤3.0%; and myristic acid (C14)≤1%.

Medium-chain triglycerides for use in preferred compositions comprise a mixture of triglycerides with fatty acid chains present in the following proportions: C6≤5%; C8 50-70%; C10 30-50%; and C12≤12%, for example C6≤0.5%; C8 55-65%; C10 35-45%; and C12≤1.5%.

Medium-chain triglycerides used in the preferred compositions may be derived from any known or otherwise suitable source.

Compositions used in the methods of the present disclosure may, advantageously, comprise one or more phospholipids. A particularly preferred phospholipid is phosphatidylcholine. The advantages brought about by phosphatidylcholine may be due, at least in part, to their amphipathic nature, e.g., due to properties as an emulsifier.

A particularly useful source of phospholipids, in particular phosphatidylcholine, is lecithin, and compositions used in the methods of the present disclosure advantageously comprise lecithin. Lecithin, when present in compositions, typically makes up at least 0.5% w/w of the composition, preferably at least 1% w/w of the composition. The lecithin preferably makes up 10% w/w or more of the composition, for example 20% w/w or more by weight, for example 30% w/w or more by weight of the composition. For example the lecithin may make up 0.5-80% w/w of the composition, for example 1-80% w/w, for example 20-80% w/w, for example 40-80% w/w, alternatively for example 0.5-75% w/w of the composition, for example, 1-40% w/w of the composition, for example 30-40% w/w of the composition, for example 30-35% w/w of the composition, for example, 30-75% w/w of the composition. Alternatively, the lecithin may make up 0.5-5% w/w of the composition, for example 1-5% w/w of the composition, for example 1-3% w/w of the composition, for example, 0.5-2% w/w of the composition, for example, 1-2% w/w of the composition. The weight ratio between the lecithin, when present, and the urolithin is generally in the range 0.02:1 to 3:1, for example, 0.03:1 to 1.2:1, for example 1:1 to 1.2:1, for example 1.1:1 to 1.2:1.

'Lecithin' designates any group of fatty substances occurring in animal and plant tissues including phosphoric acid, choline, fatty acids, glycerol, glycolipids, triglycerides, and phospholipids (e.g., phosphatidylcholine, phosphatidylethanolamine, and phosphatidylinositol). Commercial lecithin obtained from soya and sunflower comprises the phospholipids phosphatidyl choline, phosphatidyl inositol, phosphatidyl ethanolamine, and phosphatidic acid. Lecithin may be obtained by chemical extraction from its source in a non-polar solvent such as hexane, ethanol, acetone, petroleum ether or benzene, or by mechanical extraction. In particular, lecithin may be obtained by extraction from sources including soybeans, eggs, milk, rapeseed, cottonseed and sunflower. Commercial lecithin for use in edible formulations may be readily purchased.

Commercially produced lecithin, which may be used in compositions described herein, typically contains the following major components: 33-35% soybean oil, 20-21% inositol phosphatides, 19-21% phosphatidylcholine, 8-20% phosphatidylethanolamine, 5-11% other phosphatides, 5% free carbohydrates, 2-5% sterols and 1% moisture.

Commercially produced lecithin, which may be used in compositions described herein, may for example be enriched with phosphatidylcholine, having a minimum of 5% w/w phosphatidylcholine in the lecithin, for example, having a minimum of 10% w/w phosphatidylcholine in the lecithin, for example, having a minimum of 15% w/w phosphatidylcholine in the lecithin, for example, having a minimum of 20% w/w phosphatidylcholine in the lecithin, for example, having a minimum of 25% w/w phosphatidylcholine in the lecithin, for example, having a minimum of 30% w/w phosphatidylcholine in the lecithin, for example, having a minimum of 32% w/w phosphatidylcholine in the lecithin, for example, having a minimum of 40% w/w phosphatidylcholine in the lecithin.

Lecithins may also be modified by one or more of the following processes to tailor their properties: alcohol extraction of particular phospholipids to produce a lecithin with a modified ratio of differing phospholipids; acetone extraction to remove oil, resulting in a powdered or granulated phospholipid blend; spray drying onto proteins as carriers; spray cooling with synthetic emulsifiers such as high melting mono- and di-glycerides to produce flaked or powdered products; modification by enzyme action (phospholipases, commonly in particular phospholipase A2), in particular partial hydrolysis to produce lecithins with pronounced emulsifying behaviour; hydrolysis of fatty acid groups by acids and alkali; acetylation; and hydroxylation of fatty acid chains and amino groups.

In some embodiments, the methods comprise administration of a composition comprising a compound of formula (I) or salt thereof, a medium chain triglyceride, and an emulsifier (e.g., lecithin).

Pharmaceutical compositions containing the compound of formula (I) or salt thereof may for example include additional pharmaceutically active compounds.

Additional components in a composition may be compounds that do not provide health benefits to the subject, but instead improve the composition in some other way, for example its taste, texture or shelf-life as mentioned above. The composition may thus further contain one or more compounds selected from emulsifiers, colorants, preservatives, gums, setting agents, thickeners, sweeteners and flavourings.

Suitable emulsifiers, stabilisers, colorants, preservatives, gums, setting agents and thickeners are well known in the art of manufacture of emulsions and other semi-liquids. Emulsifiers may include one or more of phosphatidylcholine, lecithin, polysorbates such as polysorbate 60 or polysorbate 80 (Tween-60 and Tween-80), and glycerol monostearate (GMS). Glycerol monostearate is also known as glyceryl monostearate.

Stabilisers may be used in a composition described herein. Many compositions are stable suspensions without the need for an added stabiliser. A stable suspension is one that does not undergo a phase separation over time. For certain compositions, the stability can be improved by inclusion of an added stabiliser. Suitable stabilisers for use in compositions of the invention include glycerol monostearate (GMS), silicon dioxide and vegetable shortening. An exemplary stabiliser is GMS and preferred compositions of the invention contain GMS. Its properties also make GMS a good solvent for phospholipids, such as found in lecithin for example. GMS exists in two polymorphs: the α-form is dispersible and foamy, useful as an emulsifying agent or preservative. The β-form is suitable for wax matrices. The α-form is converted to the β-form when heated at 50° C.

GMS falls into two distinct grades: 40-55 percent monoglycerides, and 90 percent monoglycerides. 40-55 percent monoglycerides as defined by the European Pharmacopoeia describes GMS as a mixture of monoacylglycerols, mostly monostearoylglycerol, together with a quantity of di- and tri-glycerols. In particular, the 40-55 grade contains 40-55% monoacylglycerols, 30-45% diacylglycerols, and 5-15% of triacylglycerols. The 99 percent grade contains not less than 90% of monoglycerides. The monoglycerides in commercial GMS products are mixtures of variable proportions of glyceryl monostearate and glyceryl monopalmitate. The European Pharmacopoeia further divides glyceryl monostearate 40-55 into three types according to the proportion of stearic ester in the mixture. Type 1 contains 40.0-60.0% stearic acid, and the sum of palmitic and stearic acids is ≤90%. Type 2 contains 60.0-80.0% stearic acid, and the sum of palmitic and stearic acids is ≤90%. Type 3 contains 90.0-99.0% stearic acid, and the sum of palmitic and stearic acids is ≤96%. Any form of GMS may be used in the compositions.

In some embodiments, the method comprises administration of a composition comprising a medium chain triglyceride, the compound of formula (I) or a salt thereof (e.g. urolithin A), and a stabiliser, for example glycerol monostearate. In some embodiments the method involves administration of a composition comprising an emulsifier and a stabiliser.

Metal chelators or sequestrants such as sodium calcium salts of ethylenediamine tetra acetic acid (EDTA) may also be used. Other components that may be included in formulations of the invention include polyethylene glycols, silicon dioxide, vegetable shortening and beeswax.

A flavouring may be beneficial in compositions used in the methods described herein. In a liquid or semi-liquid composition, fruit flavour can be provided for example by inclusion of a fruit sauce or puree. Typical flavourings include strawberry, raspberry, blueberry, apricot, pomegranate, peach, pineapple, lemon, orange and apple. Generally, fruit flavourings include fruit extract, fruit preserve or fruit puree, with any of a combination of sweeteners, starch, stabilizer, natural and/or artificial flavours, colourings, preservatives, water and citric acid or other suitable acid to control the pH.

A unit dose composition used in the methods described herein preferably contains 250 mg or 500 mg of the compound of formula (I), for example 250 mg or 500 mg of urolithin A. A unit dose may for example be in the form of a snack bar, e.g., of weight in the range of from 25 g to 150 g, in the form of a drink provided in a container such as a bottle or pouch sufficient to hold a single dose (e.g., 50 to 500 ml, 100 to 300 mL, for example, 250 ml or 500 ml). In a further alternative example, which is preferred, the unit dose is in the form of a softgel capsule, e.g., containing 250 mg of urolithin A.

A representative composition is shown in the Table below:

Representative Composition A:

| Composition | Per 100 g |
|---|---|
| Medium Chain Triglycerides | 10-85 g |
| Urolithin A | 10-50 g |
| Lecithin (comprising minimum phosphatidylcholine content of 32% w/w) | 10-50 g |
| Glycerol Monostearate | 0-5 g |

The invention further provides a composition comprising a compound of formula (I) and a vaccine and optionally one or more additional immune enhancers and/or one or more pharmaceutically acceptable excipients. In one embodiment, the components of the composition are provided separately. In another embodiment, the components are provided in admixture. In another embodiment, the vaccine is provided separately from the compound of formula (I) in admixture with one or more additional immune enhancers. In another embodiment the vaccine is provided in admixture with the compound of formula (I) and the one or more additional immune enhancers is provided separately. In another embodiment the vaccine is provided in admixture with one or more additional immune enhancers and the compound of formula (I) is provided separately.

The pharmaceutical composition may take the form of a kit of parts, which kit may comprise the composition of the invention together with instructions for use and/or a plurality of different components in unit dosage form. Therefore, in one embodiment of the invention there is provided a kit for inducing an immune response to an antigen comprising:

a first component comprising a compound of formula (I); and a second component comprising an additional immune enhancer; and optionally one or more further components comprising one or more further immune enhancers.

In a further embodiment of the invention there is provided a kit for inducing an immune response to an antigen comprising:

a first component comprising a compound of formula (I); and a second component comprising a vaccine; and optionally one or more further components comprising one or more further immune enhancers.

In a further embodiment of the invention there is provided a kit for inducing an immune response to an antigen comprising:

a first component comprising a compound of formula (I); and a second component comprising a vaccine; and a third component comprising an additional immune enhancer; and optionally one or more further components comprising one or more further immune enhancers.

In such kits of the invention, there is optionally provided instruction to describe the order and intervals for administration of the components. In one embodiment, the components are administered at the same time. In another embodiment the components are administered sequentially with one or more days or weeks between each component.

In one embodiment kits of the invention comprise a vaccine and a compound of formula (I) and optionally one or more further immune enhancers provided separately. In another embodiment kits of the invention comprise an admixture of a vaccine and a compound of formula (I) and optionally one or more further immune enhancers.

EXAMPLES

The invention will now be illustrated with respect to the following non-limiting examples.

Example 1: Preparation of Urolithin A

Urolithin A (4) was prepared in two steps starting from 2-bromo-5-methoxybenzoic acid 1 and resorcinol 2. The pure compound was obtained as a pale yellow powder.

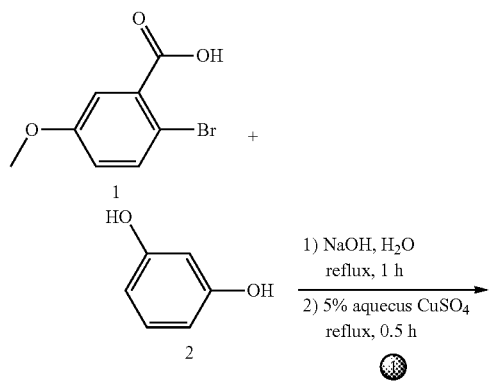

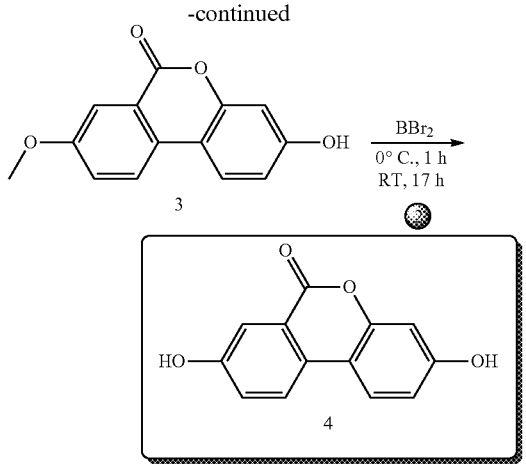

Step 1:

A mixture of 2-bromo-5-methoxybenzoic acid 1 (27.6 g; 119 mmol; 1.0 eq.), resorcinol 2 (26.3 g; 239 mmol; 2.0 eq.) and sodium hydroxide (10.5 g; 263 mmol; 2.2 eq.) in water (120 mL) was heated under reflux for 1 hour. A 5% aqueous solution of copper sulphate (3.88 g of $CuSO_4.5H_2O$ in 50 mL water; 15.5 mmol; 0.1 eq.) was then added and the mixture was refluxed for additional 30 minutes. The mixture was allowed to cool to room temperature and the solid was filtered on a Büchner filter. The residue was washed with cold water to give a pale red solid which was triturated in hot MeOH. The suspension was left overnight at 4° C. The resultant precipitate was filtered and washed with cold MeOH to yield the title compound 3 as a pale brown solid.

Step 2:

To a suspension of 3 (10.0 g; 41 mmol; 1.0 eq.) in dry dichloromethane (100 mL) was added dropwise at 0° C. a 1 M solution of boron tribromide in dry dichloromethane (11.93 mL of pure $BBr_3$ in 110 mL of anhydrous dichloromethane; 124 mmol; 3.0 eq.). The mixture was left at 0° C. for 1 hour and was then allowed to warm up to room temperature. The solution was stirred at that temperature for 17 hours. Then ice was added thoroughly to the mixture. The yellow precipitate was filtered and washed with cold water to give a yellow solid which was heated to reflux in acetic acid for 3 hours. The hot solution was filtered quickly and the precipitate was washed with acetic acid, then with diethyl ether to yield the title compound 4 as a yellow solid. $^1H$ and $^{13}C$ NMR were in accordance with the structure of 4.

Example 2: Urolithin a Dosage Form

Urolithin A was formulated into a soft gel capsule containing the following components:

| Fill | | |
|---|---|---|
| Ingredients | Amount (mg)/Cap | % Total |
| Urolithin A | 250 | 22.73% |
| Lecithin NF (35% Total PC) (Epikuron 135 F IP) - E322 | 284.25 | 25.84% |
| Medium Chain Triglycerides (MCT) | 284.25 | 25.84% |
| Glycerol Monostearate (40-55) EP, Mono- and Diglycerides NF | 11.5 | 1.06% |
| Fill Weight | 830 mg | 75.47% |

| Shell | | |
|---|---|---|
| Ingredients | Amount (mg)/Cap | % Total |
| Gelatin EP, NF | 165.97 | 15.09% |
| Glycerol - E422 | 80.01 | 7.27% |
| Water | 21.62 | 1.96% |
| Titanium Dioxide EP - E171 | 1.96 | 0.18% |
| DualDustmaster FD&C Blue #1 (Brilliant Blue FCF - E133) | 0.234 | 0.021% |
| Sodium Copper Chlorophyllin Powder (min 95%) - E141 | 0.196 | 0.018% |
| Shell Weight | 270 mg | 24.539% |
| Total Capsule Weight | 1100 mg | 100% |

Example 3: Effect of Urolithin a on Stem Cell Populations

To determine if Urolithin A treatment had any effects on stem cell populations, haematopoietic stem cells, (HSCs) and multipotent progenitor cells (MPPs) were isolated from aged C57BL/6J mice that received either a standard rodent diet or a diet containing Urolithin A mixed with food to reach a dosing of 50 mg/kg/day delivered to mice. Mice were treated with urolithin A starting at 16 months of age and received 34 weeks of treatment. At end of the treatment period mice were sacrificed and bone marrow collected from the femur and tibia bones. Single-cell suspensions were made following cell extraction from the bones after removal of muscle and connective tissue.

To determine the effects of Urolithin A treatment on the different progenitor cells of the haematopoietic system, the number and percentage of each progenitor cell type was determined using flow cytometry. Flow cytometry allowed the selection and quantification of cells with different patterns of protein expression on their cell surface. Using labeled monoclonal antibodies, it was possible to identify the different progenitor cell population based on their cell surface protein expression. To isolate the undifferentiated cells which would contain the progenitor population, bone marrow cells were stained with a cocktail of monoclonal antibodies against the cell surface proteins specific to the more differentiated cell types. The antibodies to these proteins, also known as lineage markers were CD3e (17A2), CD4 (GK1.5), CD8a (53.6.7), CD11b (M1/70), CD19 (1D3), Gr1 (RB6.8C5), Ter119 and NK1.1 (PK136), these were conjugated to Alexa 647 [Alexa Fluor 647 dye is a bright, far-red—fluorescent dye used as a label in, for example, fluorescence microscopy]. To discriminate the various lineage progenitor cell populations the isolated bone marrow cells were stained with monoclonal antibodies against the following progenitor cell surface protein markers containing the following labels CD34 (RAM 34)-FITC; CD135 (Flt3 A2F10)-PE; CD48 (HM48.1)-biotin+PE Texas Red Streptavidin; CD117 (ckit 2B8) PerCp-Cy5.5; Sca1 (D7)-PE-Cy7. Cell analysis of the stained cells was performed on a Becton Dickson Flow cytometer (Franklin Lake, NJ, USA) and collected data was analyzed using Flowjo™ software (an analysis platform for single-cell flow cytometry analysis). Bone marrow was isolated from three mice receiving Urolithin A treatment, and six control untreated mice.

Figure 2:
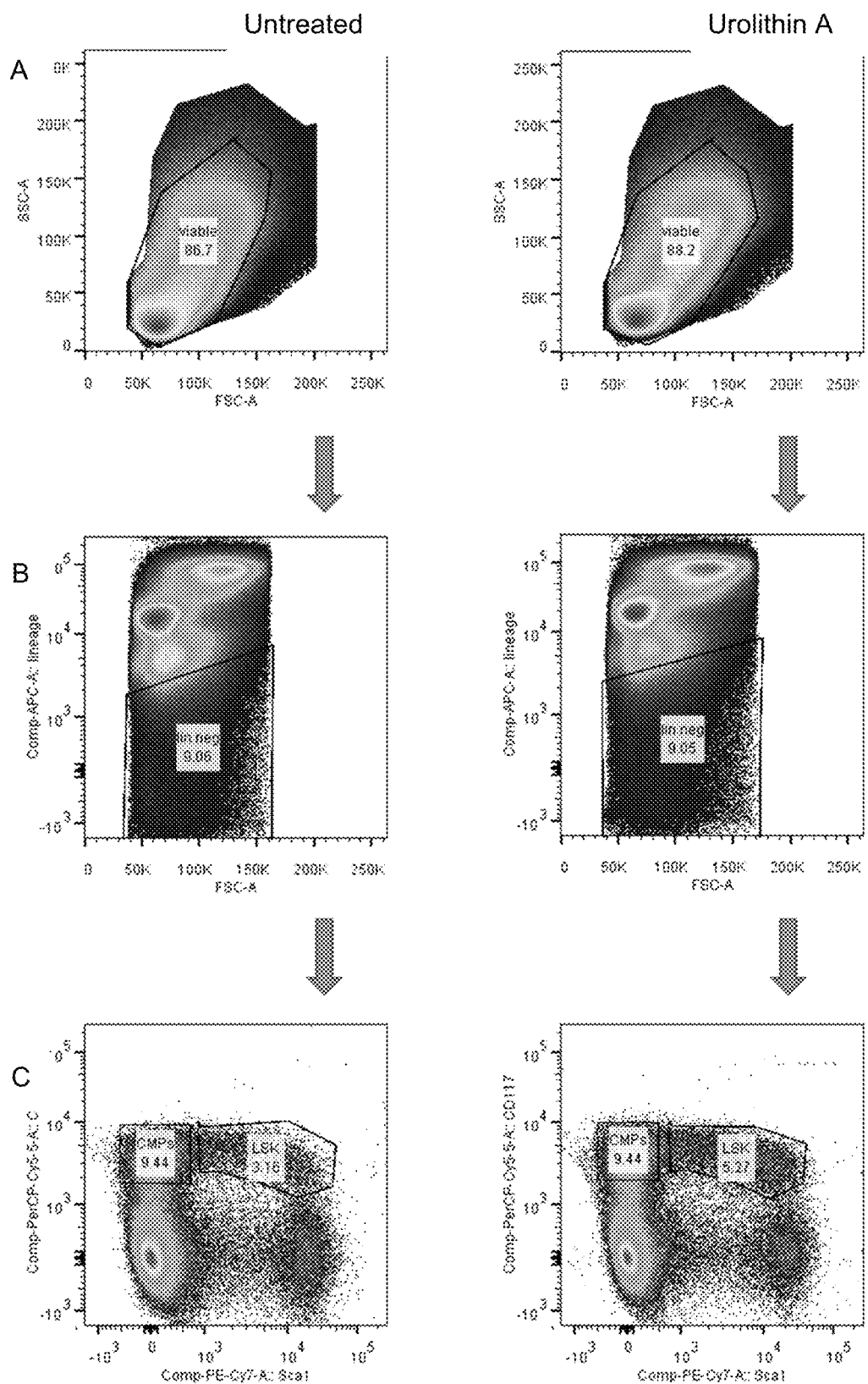
FIG. 2 is a set of plots of bone marrow cells isolated from aged C57BL/6J mice analysed by flow cytometry. The plots demonstrate an example of the gating strategy used to select the population containing the progenitor cells, LSK (c-Kit+, Lin−, Sca 1+) cells. In this particular example, Urolithin A treatment leads to a substantial increase in the population of progenitor cells, from 3.16% of lineage negative cells in control mice, to 5.27% in aged mice treated with Urolithin A.
Figure 3:
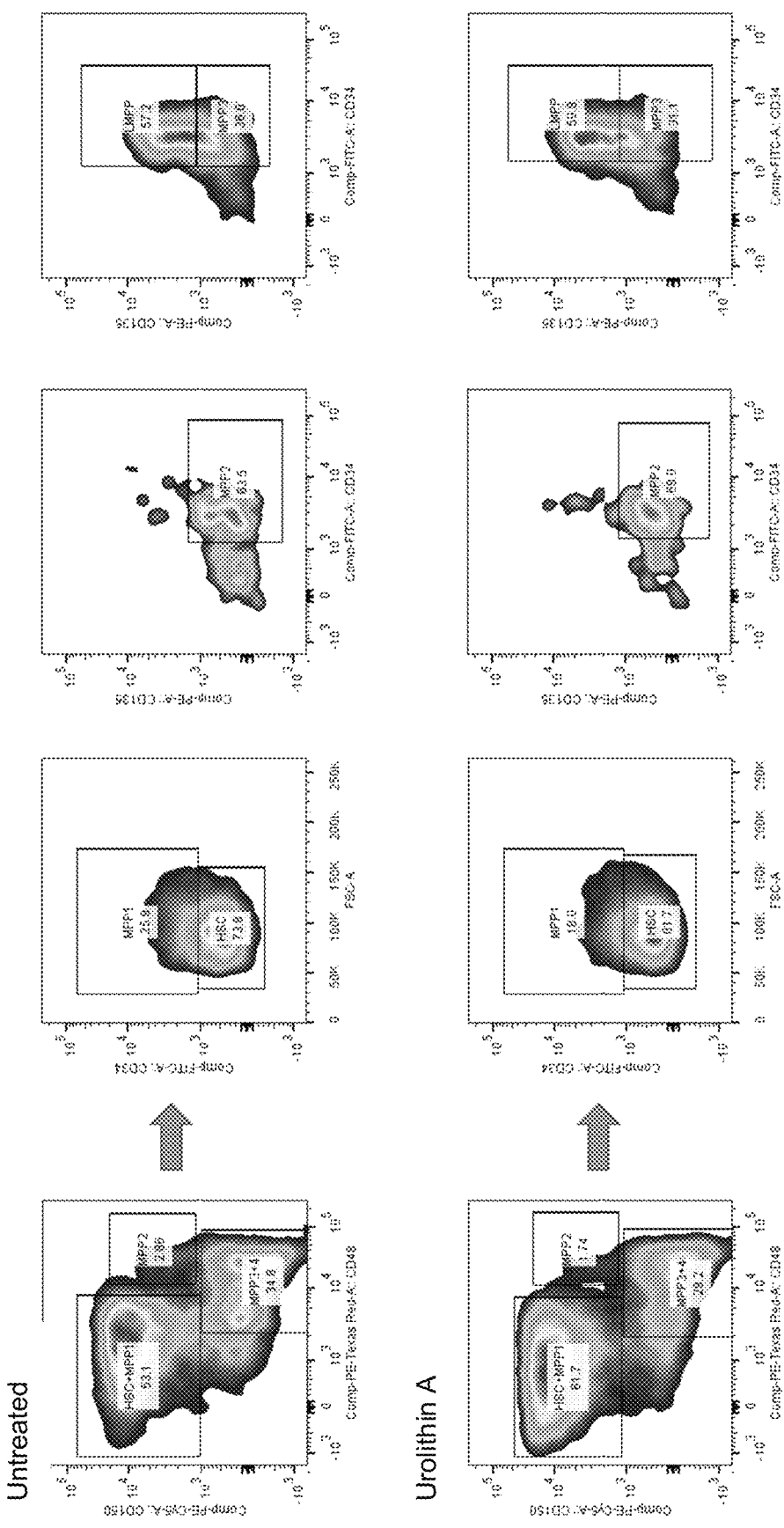
FIG. 3 shows the gating strategy used to select the different progenitor populations, as well as the effects of Urolithin A treatment on these different haematopoietic progenitor cell populations. The different progenitor populations present in the LSK (c-Kit+, Lin−, Sca 1+) populations of cells were separated on the bases of their expression of CD150, CD48, CD34, and CD135. Urolithin A treatment results in an increase in the % of LSK cells that are the most non-committed progenitor cells (HSC+MPP1) from 53.1% to 61.7%. This increased population of HSC+MPP1 progenitor cells is further enriched for HSC cells, from 73.8% (untreated) to 81.7% (Urolithin A).

To identify the different populations of haematopoietic progenitor cells present in the isolated bone marrow cells, the isolated bone marrow cells were selected based on their cell surface marker combinations. A so-called gating strategy was employed, in which a particular population of cells is selected (gated) based on the pattern of cell surface protein expression, and then this sub-selected population then is further examined for its cell surface protein expression. FIGS. 2 and 3 demonstrate an example of the gating strategy that was employed on all the samples examined. Uncommitted progenitor cells were examined by selecting cells that were negative for the cell surface proteins found on differentiated cells (lineage markers) described above (FIG. 2B). From this population of lineage negative cells, cells were selected that stained positive for the cells surface markers, CD117 (c-kit) and Sca1. This subpopulation of lineage negative, CD117 & Sca1 positive cells (LKS cells) contain the progenitor stem cells (FIG. 2C). FIG. 2C shows that in aged animals receiving Urolithin A treatment there is a substantial increase in the population of LKS progenitor cells present in the lineage negative cells, from 3.16% in control-treated aged mice, to 5.27% in aged mice treated with Urolithin A.

Figure 1B:
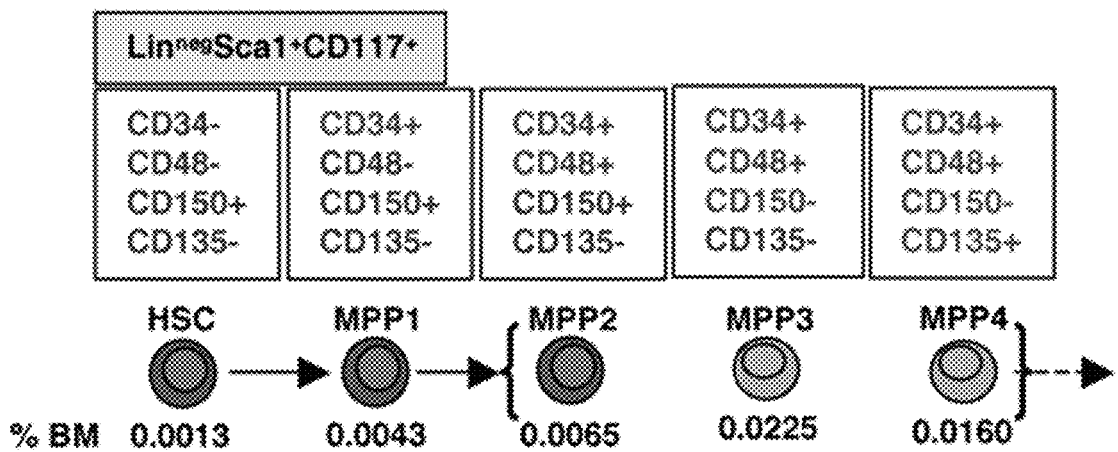
FIG. 1B describes the cell surface markers which can be utilized to define the different subpopulations of progenitor cells and the relative contribution of each population to the total bone marrow (% BM). In humans, a similar set of human protein markers have been identified, for both HSC ($Lin^-CD34^+CD38^-CD45RA^-CD90^+CD49^+$) and MPPs ($Lin^-CD34^+CD38^-CD45RA^-CD90^-CD49f^-$). The Haematopoietic stem cell (HSC) is the most quiescent cell and the source for the different multipotent progenitor cells (MPPS).
Figure 4:
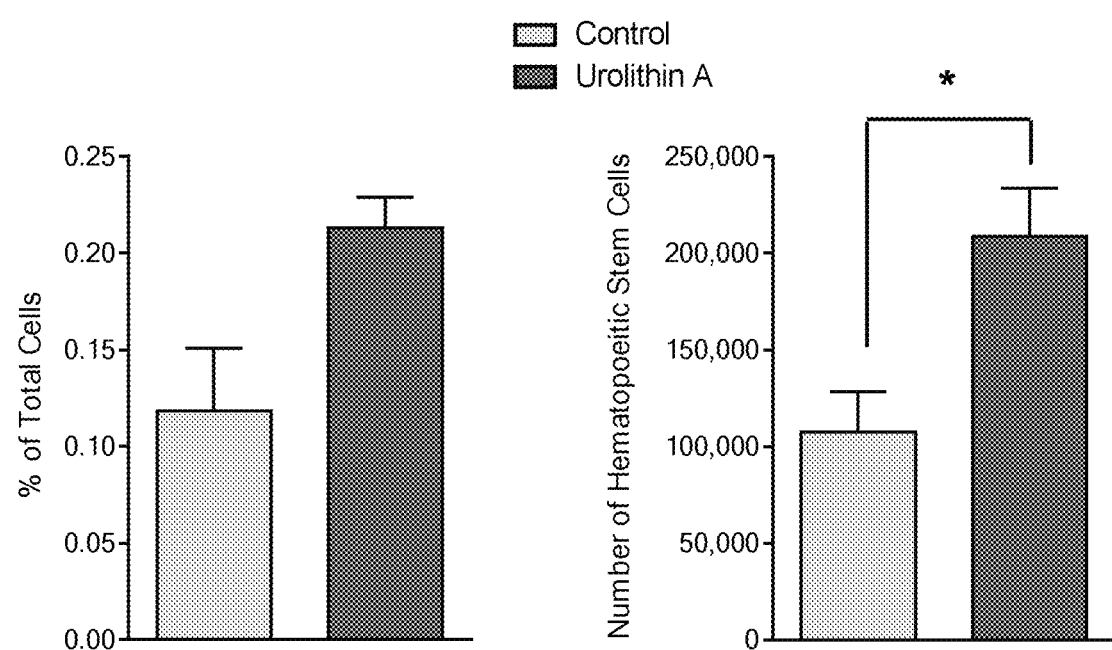
FIG. 4 demonstrates the effect of Urolithin A on the most primitive haematopoietic stem cell population. Urolithin A treatment in aged animals resulted in an increase in the most primitive progenitor haematopoietic stem cell (HSC) population as both a % of total cells and number of cells. The increase in the number of total stem cells is statistically significant, $p<0.05$.
Figure 5:
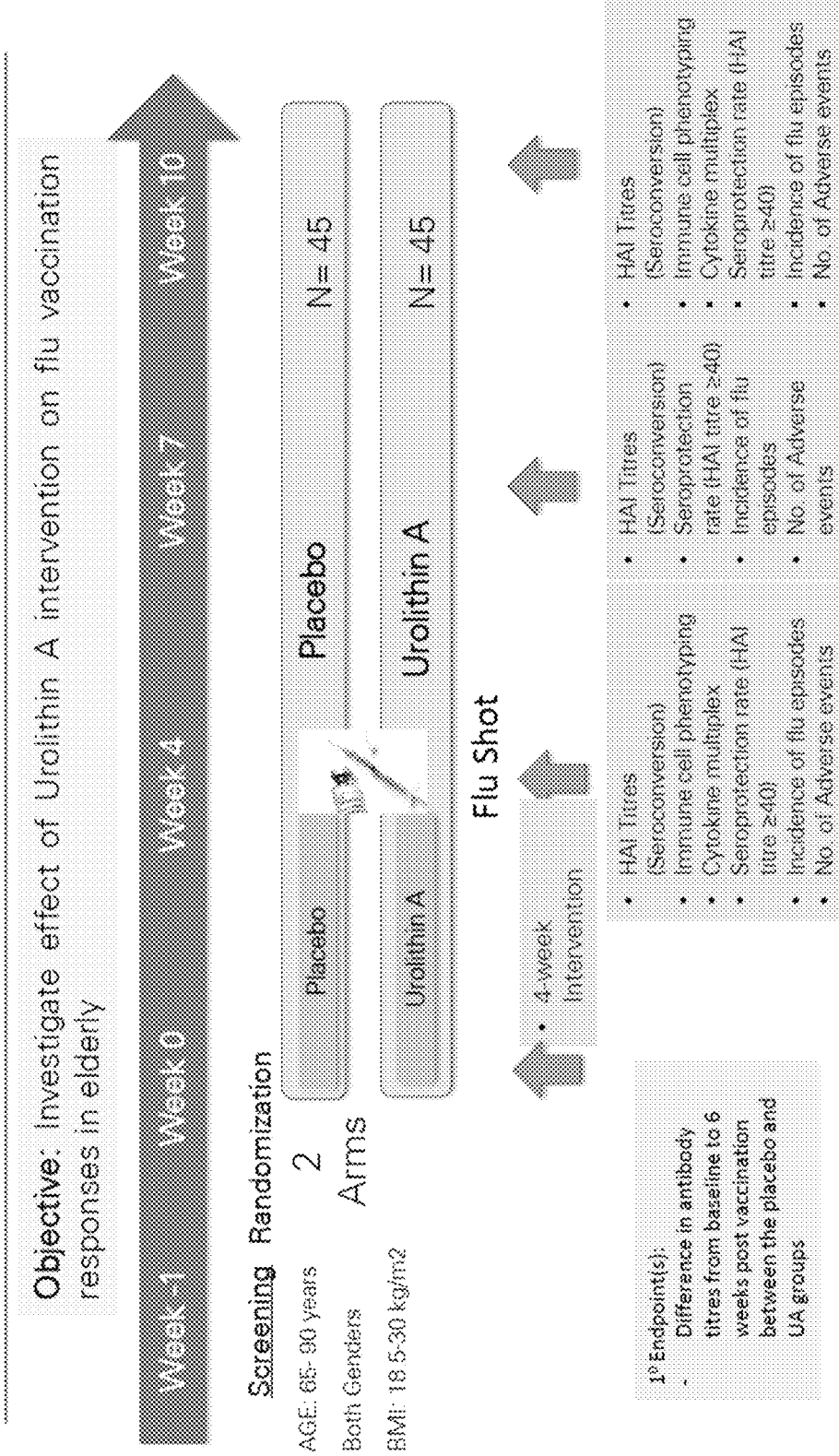
FIG. 5 shows the design of a Phase 2 clinical trial to assess the effect of urolithin A on antibody titres in response to flu vaccination.

LKS cells can be further divided into four different progenitor cell types, HSC (LT-HSC), MPP 1 (ST-HSC), MPP2, and MPP3 or LMPP with decreasing levels of quiescence (FIG. 1B). The most quiescent and non-committed cells are the HSC cells. To differentiate between these cell populations in the LKS cells, Cells were examined for their expression of CD150 and CD48. The most primitive quiescent cell populations, HSC+MPP1, are positive for the cell surface marker for CD150 and negative for the cell surface marker CD48. As shown in FIG. 3 (1st set of graphs), Urolithin A treatment results in a significant increase in this population in this example, with 61.7% of LKS cells being HSC+MPP1 cells in the treated animal, versus 53.1% in the untreated animal. This was found to be the case in all the animals treated with urolithin A (n=3) when compared to untreated mice (n=5) and the increase in this progenitor population was statistically significant (Table 2). The HSC+MPP1 progenitor cells are stem cells that are able to reconstitute all the different blood cell lineage populations. The HSC+MPP1 progenitor cells can be further subdivided into two different types of haematopoietic stem cells, a long-term renewing population (HSC or LT-HSC), which enters the cell cycle less frequently and serves to maintain the stem cell population, and another population, MPP1 or ST-HSC, which cycles more frequently and is responsible for maintaining the blood cell lineages. These two populations can be discriminated by selecting (gating) the HSC+MPP1 cells and examining these cells for their expression of the cell surface marker CD34. The most primitive stem cell population, HSC or LT-HSC, do not express CD34 (FIG. 1B). As shown in FIG. 3 (2nd set of graphs), Urolithin A treatment results in an increase in the % of HSC+MPP1 cells that are HSC's in aged animals from 73.8% to 81.7%. Importantly, this increase in the most primitive stem cell population results in an even more pronounced increase in the final total numbers of HSC's present in the hindlimb both as a % of total bone marrow cells, as well as cell numbers, as shown in FIG. 4, with there being a significant increase in HSC cells numbers in aged animals treated with urolithin A versus aged animals that were not treated.

TABLE 2

| Cell Population | Untreated | Urolithin A | Remark |
| --- | --- | --- | --- |
| HSC + MPP1 | 40.75 ± 7.42% of undifferentiated cells (LSK cells) | 58.97 ± 11.30% of undifferentiated cells (LSK cells) | Statistically significant increase in the % of stem cells present in the bone marrow. $p < 0.01$ |

Example 4: Pre-Clinical Experiment to Assess the Improvement in Antibody Titres in Response to Vaccination after Administration of Urolithin a Experimental Outline Adult female BALB/c are randomly allocated to experimental groups and allowed to acclimatise for one week. From Day 0, animals are administered according to the schedule below by food admix. An intramuscular (i.m.) challenge with the PR8 antigen is performed on Days 0, 14 and 28. From Day 0, animals are monitored daily for non-specific clinical signs. From Day 0, animals are weighed three times per week. On Day 28, blood samples are collected to perform the Hemagglutination inhibition assay (HAI), and processed to isolate serum for analyses of antibodies (total IgG targeted against PR8).

On Day 42, spleens are dissected out, processed to single cell suspension and plated for a T cell proliferation assay. Cells are incubated in triplicate in the presence or absence of PR8 (antigen) overnight or with positive control. Ex vivo immune cells harvested from the spleens (systemic reservoir of immune cells in the body) mice treated with vehicle (group 1 in the table below) were stimulated for 24 hours with or without UA/vehicle to look at cell proliferation. Cell proliferation is the main readout in this in vitro assay to assess the enhancement of immune responses and is quantified by tritiated thymidine incorporation. Cell culture supernatants are stored for analysis of cytokines by multiplex.

Administration Schedule

All groups are n=12

| Group | Treatment | Challenge IM Day 0 Day 14 Day 28 |
| --- | --- | --- |
| 1 Vehicle | Vehicle, PO, Day 0-Day 42 | n/a |
| 2 Vehicle + PR8 | | PR8 |
| 3 Test item Dose 1 + PR8 | Test, PO, Day 0-Day 42 | PR8 |
| 4 Test item Dose 2 + PR8 | Test, PO, Day 0-Day 42 | PR8 | n/a: not applicable,
PO: administration in the diet,
PR8: antigen,
IM: intra-muscular Example 5: Phase 2 Clinical Trial to Assess the Improvement in Antibody Titres in Response to Flu Vaccination after Administration of Urolithin A A Phase 2 trial is performed to assess the effect of Urolithin A on antibody titres in elderly people in response to flu vaccination. A summary of the protocol is seen in FIG. 2.

Patients are recruited into the trial with the following main inclusion criteria:
1) 65-90 yrs old
2) both genders (males and females)
3) Body Mass Index (BMI) between 18.5-30 kg/m$^2$; and
4) the ability to give informed consent and finish the trial and its visits.

Patients are recruited with the following main exclusion criteria:
1) Planned participation during the present trial period in another clinical trial investigating vaccine or drug.
2) Receipt of any vaccine in the 4 weeks preceding the trial period.
3) Receipt of an influenza vaccine within the 6 months preceding the trial vaccination period.
4) Known or suspected congenital or acquired immunodeficiency or receipt of immunosuppressive therapy, such as anti-cancer chemotherapy or radiation therapy, within the preceding one year.
5) Systemic hypersensitivity to eggs, chicken proteins, or any of the vaccine components.
6) Current alcohol or drug addiction.
7) Chronic illness that, in the opinion of the investigator, is at a stage where it might interfere with trial conduct or completion.
8) Suffer from auditory or visual disorders.
9) Diagnosed with severe cognitive impairment (MMSE<18), or major depression.
10) Progressive neurodegenerative neurologic disease: e.g., Alzheimer's disease.
11) Hospital admission in the past 6 weeks.
12) Self-reported thrombocytopenia, contraindicating intramuscular vaccination
13) Bleeding disorder, or receipt of anticoagulants in the 3 weeks preceding vaccination, contraindicating intramuscular vaccination upon investigator's judgement.

Clinical Trial Protocol

The role of UA in boosting immune health during aging to improve vaccination responses will be assessed in a double-blind, randomized and placebo controlled clinical trial. The primary outcome of the study would be to show a statistically higher fold-change/seroconversion in post-vaccination antibody geometric mean titres (GMT) of the major flu strains (H1N1, H3N2 and type B) in the UA treated elderly group compared to those vaccinated in the placebo treated groups. Healthy elderly adults are screened based on the inclusion and exclusion criteria described above and are randomized to either a placebo group (n=45-75 subjects) or to an active group that received Urolithin A (n=45-75 subjects). Placebo and Urolithin A would be in the form of a softgel, for example. Subjects will receive the intervention for a total of four weeks following randomization. Following the four weeks of intervention with either placebo or active treatment, all the subjects will have pre-vaccination antibody titers and immune health status assessed in the serum. Subject will then be subsequently challenged with the flu vaccine and antibody titers to flu vaccination assessed again at 3 and 6 weeks in serum collected at these timepoints. The design of the clinical trial is to be performed as shown in FIG. 1.

Clinical Trial Endpoints

The primary endpoint of the clinical trial is post vaccination fold change in seroconversion (i.e., geometric mean titres of antibody responses assessed by Hemagglutination Inhibition (HAI) t to the three major virulent flu strains—H1N1, H3N2 and Type B) when comparing the placebo to UA treated The anticipated seroconversion change in UA treated when compared to placebo groups may be in the range of 40-60% when compared to placebo treated elderly group that may be in the range of 15-30% seroconversion, for example. Geometric mean titres of the major flu strains may be for example 1.5 to 2 times higher in UA treated elderly subjects compared to placebo intervention.

Key secondary endpoints can include seroprotection (incidence of being protected from flu) and cellular T cell memory responses (cytokines, T-cell memory).

Example 6: Pre-Clinical Experiment to Assess the Improvement in Anti-Inflammatory Profile after Administration of Urolithin A Urolithin A is admixed to AIN-93G Growing Rodent Diet (Research Diet, New Brunswick, NJ, USA) at a concentration of 0.5 g/per kg of diet, corresponding to a dose of 50 mg/kg/dy. Pellets with or without UA are given to 22 months old male C57BL/6J mice (Janvier, Saint Berthevin, France) for 6 weeks. A total of 32 mice are housed individually and randomized to 16 animals per group according to their exercise capacity. Animals who die spontaneously during the experiments are excluded from the calculations. These criteria were established before starting the experiments. Animals are euthanized after 6 weeks of treatment after an overnight fasting before collecting blood samples by the vena cava. Blood samples are centrifuged for 15 minutes at 1,500×g, and the plasma supernatant is transferred into a clean tube. Plasma is analyzed for cytokines using the MILLIPLEX MAP Mouse Cytokine/Chemokine Magnetic Bead Panel (MCYTOMAG-70K).

Figure 6:
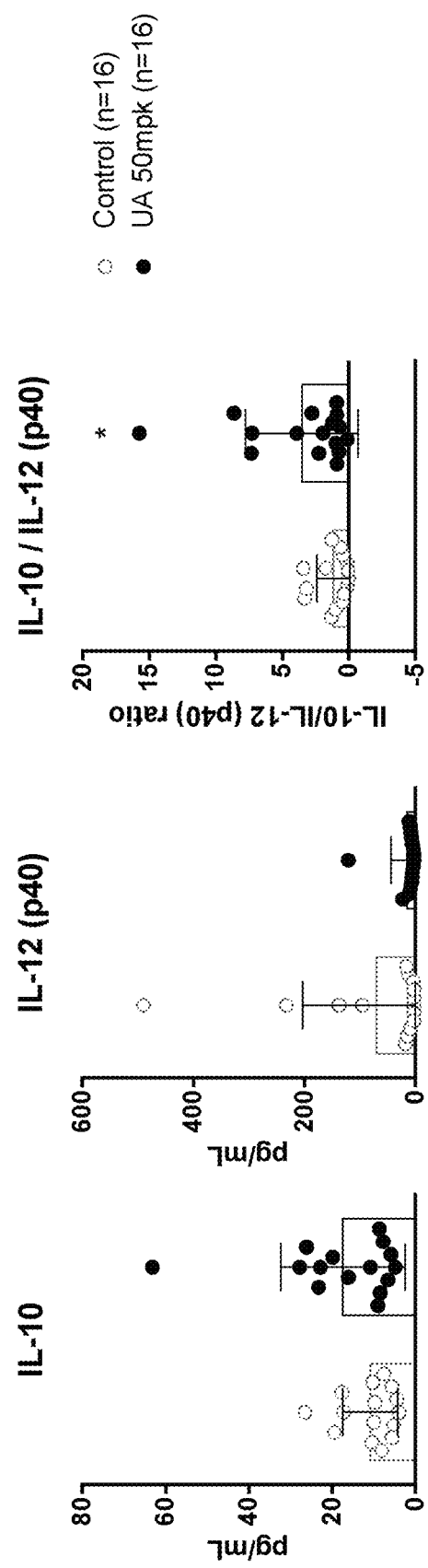
FIG. 6 demonstrates the effect of Urolithin A on pro- vs anti-inflammatory cytokines. Urolithin A treatment in aged animals resulted in a significant increase in IL-10 over IL-12 (p40) ratio ($p<0.05$).

FIG. 6 shows the results for interleukin-10 (IL-10), interleukin-12 subunit beta, also known as IL-12 (p40), and the ratio of IL-10/IL-12 (p40). IL-10 is an important anti-inflammatory cytokine (Fiorentino D F, et al., IL-10 inhibits cytokine production by activated macrophages. J Immunol. 1991 Dec. 1; 147(11):3815-22; Fiorentino D F et al., IL-10 acts on the antigen-presenting cell to inhibit cytokine production by Th1 cells. J Immunol. 1991 May 15; 146(10): 3444-51). Interleukin-12 (IL-12) is a potent proinflammatory cytokine that enhances the cytotoxic activity of T lymphocytes and resting natural killer cells. As shown in FIG. 6, there is a significant increase in the ratio of IL-10 over IL-12 (p40) ratio. This result shows that UA treatment in aged mice is able to reduce the so-known inflammageing (Daniela Frasca and Bonnie B. Blomberg Inflammageing decreases adaptive and innate immune responses in mice and humans. Biogerontology. 2016; Franceschi C et al., Inflammageing: a new immune—metabolic viewpoint for age-related diseases. Nature Reviews Endocrinology 2018) by shifting the cytokine profiles toward a more anti-inflammatory phenotype.

Example 7: Pre-Clinical Experiment to Assess the Improvement of Hair Regeneration with Urolithin A Hair is formed in the hair follicle, which is a highly proliferative tissue due to the constant renewal of stem cells and their further differentiation. These dynamic mechanisms require very elevated bioenergetic capacities, therefore there is increasing evidence pointing at the role of the mitochondria during this process, particularly during the differentiation phase (Kloepper, J. E. et al. J. Invest. Dermatol. 135, 679-689 (2015)). Human stem cells derived from the human follicle mainly rely on aerobic glycolysis for energy generation (Kealey, Williams R, P. M. Ski. Pharmacol. 7, 41-46 (1994)), however upon differentiation they switch towards oxidative phosphorylation (OXPHOS) which totally depends on the mitochondrial function (Tang, Y. et al. PeerJ 4, e1821 (2016); Hamanaka, R. B. et al. Sci. Signal. 6, (2014)).

C57BL6/J male, 3 months old mice are used in this study. Dorsal skin hair in the telogen phase are carefully depilated. For more details regarding hair phase identification please refer to Müller-Röver, S. et al. *A comprehensive guide for the accurate classification of murine hair follicles in distinct hair cycle stages*. J. Invest. Dermatol. 117, 3-15 (2001). Animals are randomly assigned to three different experimental groups. One day after epilation, 100 µl of placebo control, UA concentration 1 and UA concentration 2 are daily applied to the region of interest (appropriated UA formulations will be previously determined). In order to quantify the extent of hair growth, the region in the mice back is daily imaged and further analyzed with the NIH ImageJ software (https://imagej.nih.gov/ij/). The level of pigmentation of the region is measured taking into consideration the background color of mouse skin. Mice are sacrificed after 0, 7, 15 and 30 days of treatment. Skin is collected, placed in cryomolds with Optimal Cutting Temperature (OCT) compound and frozen at −80° C. for further histological analysis.

In order to analyze the cycle of hair follicle regeneration, frozen skin sections are longitudinally sectioned using cryostat and stained with hematoxylin and eosin. Images are acquired on an Olympus microscope. To quantify the hair cycle, individual hair follicles of each mouse are classified based on the guidelines (Müller-Röver, S. et al. *A comprehensive guide for the accurate classification of murine hair follicles in distinct hair cycle stages*. J. Invest. Dermatol. 117, 3-15 (2001)). The percentage of hair follicles in specific anagen stages is calculated in each group. Hair follicles in the same area are counted in sections of each mouse. In addition, the total number of hair follicles in the same area is quantified.

Example 8a: In Vivo Testing of Urolithin A Ability to Increase the Number of Muscle Stem Cells In order to test the ability of UA to increase muscle stem cell number mouse models of muscle degeneration are used, including but not restricted to models of muscle atrophy, muscle dystrophies and other neuromuscular degenerative disorders, such as the models described more in details in the table below.

| Condition | Mouse model | Comment |
| --- | --- | --- |
| Muscle Atrophy | Cast/Velcro Immobilization | |
| Muscle Atrophy | Denervation | |
| Muscle Atrophy | Hind-limb suspension | |
| Duchenne Muscle Dystrophy | C57BL/10ScSn-Dmdmdx/J | Strain commonly referred as mdx, that do not express dystrophin. |
| Duchenne Muscle Dystrophy | B6.Cg-Terctm1Rdp Dmdmdx-4Cv/BlauJ | "Humanized" version of the mdx strain, that do not express both dystrophin and telomerase. |

Mice are fed with standard diet with or without UA, at a dose ranging between 10 mpk/d and 250 mpk/d. The number of animals per condition and the duration of the treatment depends on the model used. At the end of the experiment, mice are euthanized and muscles are collected and digested with type II collagenase (Sigma) and collagenase/dispase (Roche). Muscle slurries are then filtered through cell strainers and the isolated cells are washed and stained with antibodies, including the MuSC (muscle stem cell) markers CD31 (1:800, eBioscience, eFluor450 conjugated); CD45 (1:200, eBioscience, eFluor450 conjugated); Sca-1 (1:1000, eBioscience, PE-Cy7 conjugated); and VCAM-1 (1:200, MBL) for 40 min at 4° C. Secondary staining is performed with propidium Iodide (PI, Sigma). Stained cells are analysed and sorted using the FACSAria II instrument (BD Biosciences). Muscle stem cells are defined as CD31 negative, CD45 negative, SCA negative, VCAM positive muscle stem cells. Debris and dead cells are excluded by forward scatter, side scatter and PI gating.

Example 8b: In Vivo Testing of Urolithin A to Increase the Number of Muscle Stem Cells in Old Mice Middle-aged and old male C57BL/6 mice are fed with pellets of standard chow diet with or without UA and the assessment of muscle stem cell number is performed as described in Example 8a.

Example 8c: Ex Vivo Testing of Urolithin A to Increase the Number of Muscle Stem Cells Muscles from C57BL/10ScSn-Dmd$^{mdx}$J mice and 20-month-old male C57BL/6 mice are isolated, washed and digested in a Collagenase solution. Single myofibers are released using a glass pipette and treated with DMSO or UA (at a final concentration ranging between 50M and 100 □M) for different time frames and stained for muscle stem cell markers. Microscopy images are acquired by confocal microscopy and the number of muscle stem cells per myofiber is determined using the ImageJ software.

Example 9: Ex Vivo Testing of Urolithin a to Increase the Number of Inner Hair Progenitor Cells The *cochleae* from neonatal mice (postnatal days 1-3) are dissected in Hank's balanced salt solution (HBSS), and the organ of *Corti* (sensory epithelium) is separated from the *stria vascularis* (ion transport epithelium) and the modiolus (nerve tissue). The organs of *Corti* are then treated with Cell Recovery Solution (Corning) for 1 hr to separate cochlear epithelium from the underlying mesenchyme. Epithelia are then collected and treated with TrypLE (Life Technologies) for 15-20 min at 37° C. Single cells obtained by mechanical trituration are filtered (40 mm) and suspended in a Matrigel (Corning) dome for 3Dculture. Cells are bathed in a serum free 1:1 mixture of DMEM and F12, supplemented with Glutamax (GIBCO), N2, B27 (Invitrogen), EGF (50 ng/mL;

Chemicon), bFGF (50 ng/mL; Chemicon), IGF-1 (50 ng/mL; Chemicon), and DMSO or UA. Media were changed every other day.

To differentiate stem cell colonies, the expansion media is removed and colonies remained in 3D culture. A serum-free 1:1 mixture of DMEM and F12, supplemented with Glutamax (GIBCO), N2, and B27, (Invitrogen) and DMSO or UA is used to test the effect of the compound on differentiation.

To evaluate the impact of UA on inner hair progenitor cells proliferation, cells that are positive for Lgr5 are quantified after 10 days in culture in multiple conditions. Cell colonies are dissociated into single cells using TrypLE (GIBCO). Cell counting is performed with a hemocytometer. The cells are then stained with propidium iodide (PI) and analyzed using a flow cytometer for Lgr5 expression.

To quantify hair cell production and evaluate the impact of UA on inner hair progenitor cells differentiation, cells that are positive for Atoh1 are quantified at day 0 and day 10 of differentiation treatment. Cell colonies are incubated in Cell Recovery Solution (Corning) to release the colonies from Matrigel and dissociated into single cells using TrypLE. The total number and percentage of Atoh1+ cells is quantified by FACS.

Example 10. UA Induces Neural Stem Cells Proliferation and Differentiation

Several central nervous system (CNS) diseases are characterized by the neuronal loss in specific areas of the brain, therefore there is an increasing interest in identifying therapeutic strategies to repopulate the damaged areas with functional neurons. One attractive approach is the use of neural stem cells (NSC). NSC are undifferentiated cells with the capacity of self-renew and differentiate into neurons, astrocytes and oligodendrocytes. These cells are key players during the development of CNS and for the maintenance of adult brain. NCS can be isolated from the embryonic brain of mammals which allows to study strategies to modulate their proliferation and differentiation into mature neurons (Marsh, S. E. & Blurton-Jones, M. Neurochem. Int. 106, 94-100 (2017)).

Proliferation assay: To evaluate the effect of UA on NSC proliferation and differentiation embryonic rat NSC are used. Rat NSCs are isolated following standard procedures (Zhenxian Han, Qian Xu, Changfu Li, H. Z. Genesis 55, (2017)). Sprague-Dawley pregnant rats are euthanized following isoflurane overdose and embryonic brain from rat was collected on gestational day 16. Cortices are removed, mechanically dissociated in Hank's medium (calcium and magnesium-free) and then are centrifuged for 10 min at 1000 rpm. The pellet is then resuspended in Dubelcco's modified Eagle's medium (DMEM). Cultures are maintained in DMEM/F12 supplemented with N2, EGF/BFGF (10 ng/mL), and PDGF/NT3 (5 ng/mL). NSC cells are plated in a 96 well plate format, at the density of 30000 cells/well.

Proliferation assay: To test the effect of UA on NSC proliferation the neurosphere formation assay is used. Cells are seeded in culture medium and after the determined treatments the neurospheres are stained with Ki-67 antibody which specifically labels proliferating cells. Images are acquired using al Olympus microscope and the number of Ki-67 positive cells are quantified in a blinded manner.

Differentiation assay: In order to assay the effect of UA on NSC differentiation into neurons, cells are seeded in 6-well plates. After UA treatment, cells are stained with an antibody against the neuronal marker Tuj-1, followed by adding second antibody. Images are acquired using an Olympus microscope and the number of Tuj-1 positive cells are quantified in a blinded manner.

INCORPORATION BY REFERENCE

All of the U.S. patents and U.S. and PCT patent application publications cited herein are hereby incorporated by reference.

EQUIVALENTS

Those skilled in the art will recognize, or be able to ascertain using no more than routine experimentation, many equivalents to the specific embodiments of the invention described herein. Such equivalents are intended to be encompassed by the following claims.

We claim:

1. A method of vaccination comprising:
   a) administering to a subject in need of vaccination an effective amount of a compound of formula (I)

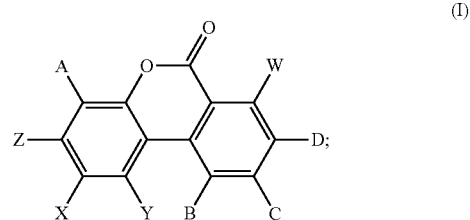

and
   b) administering to the subject a vaccine;
      wherein the subject is a human or an animal;
      A, B, C, D, W, X, Y and Z are each independently selected from H and OH;
      or a salt thereof.

2. The method of claim 1, wherein A, C, D and Z are independently selected from H and OH; and B, W, X and Y are all H.

3. The method of claim 1, wherein the compound of formula (I) is selected from urolithin A, urolithin B, urolithin C and urolithin D.

4. The method of claim 1, wherein the compound of formula (I) is urolithin A.

5. The method of claim 1, wherein an immune function or immune health of the subject is improved.

6. The method of claim 5, wherein A, C, D and Z are independently selected from H and OH; and B, W, X and Y are all H.

7. The method of claim 5, wherein the compound of formula (I) is selected from urolithin A, urolithin B, urolithin C and urolithin D.

8. The method of claim 5, wherein the compound of formula (I) is urolithin A.

9. The method of claim 1, wherein the subject is an elderly human person or child.

10. The method of claim 9, wherein A, C, D and Z are independently selected from H and OH; and B, W, X and Y are all H.

11. The method of claim 9, wherein the compound of formula (I) is selected from urolithin A, urolithin B, urolithin C and urolithin D.

12. The method of claim 9, wherein the compound of formula (I) is urolithin A.

13. The method of claim 1, wherein the subject is an elderly human aged 60 years or older.

14. The method of claim 13, wherein A, C, D and Z are independently selected from H and OH; and B, W, X and Y are all H.

15. The method of claim 13, wherein the compound of formula (I) is selected from urolithin A, urolithin B, urolithin C and urolithin D.

16. The method of claim 13, wherein the compound of formula (I) is urolithin A.

17. The method of claim 1, wherein the subject is immunocompromised.

18. The method of claim 17, wherein A, C, D and Z are independently selected from H and OH; and B, W, X and Y are all H.

19. The method of claim 17, wherein the compound of formula (I) is selected from urolithin A, urolithin B, urolithin C and urolithin D.

20. The method of claim 17, wherein the compound of formula (I) is urolithin A.

\* \* \* \* \*